US 6,539,945 B2

(12) United States Patent
Cosgrove

(10) Patent No.: US 6,539,945 B2
(45) Date of Patent: *Apr. 1, 2003

(54) MINIMALLY INVASIVE CARDIAC SURGERY PROCEDURE

(75) Inventor: Delos M. Cosgrove, Hunting Valley, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/770,519

(22) Filed: Jan. 25, 2001

(65) Prior Publication Data

US 2001/0003986 A1 Jun. 21, 2001

Related U.S. Application Data

(63) Continuation of application No. 08/801,494, filed on Feb. 18, 1997, now Pat. No. 6,182,664, which is a continuation-in-part of application No. 08/603,313, filed on Feb. 19, 1996, now Pat. No. 5,752,526.

(51) Int. Cl.[7] .............................................. A61B 19/00

(52) U.S. Cl. ..................................................... 128/898

(58) Field of Search ........................................ 128/898

(56) References Cited

U.S. PATENT DOCUMENTS

| 1,944,009 A | 1/1934 | Homer |
| 4,239,036 A | 12/1980 | Krieger |
| 4,380,999 A | 4/1983 | Healy |
| 4,889,137 A | 12/1989 | Kolobow |
| 5,041,130 A | 8/1991 | Cosgrove et al. |

(List continued on next page.)

FOREIGN PATENT DOCUMENTS

| DE | 3127830 | 7/1980 |
| FR | 2570266 | 3/1986 |
| WO | WO 93/01768 | 2/1993 |
| WO | WO 93/18712 | 9/1993 |
| WO | WO 94/18881 | 9/1994 |

(List continued on next page.)

OTHER PUBLICATIONS

J. Card Surg., 1995, 1995, 10:529–536, M. Clive Robinson, MD et al.; "Minimally Invasive Coronary Artery Bypass Grafting: A New Method Using an Anterior Mediastinotomy".

The Second Department of Surgery, Yamaguta University School of Medicine, vol. 48, No. 4, 1995—"Partial Median Sternotomy 1,2,3"; Hideaki Uchino et al.

(List continued on next page.)

Primary Examiner—Corrine McDermott
Assistant Examiner—Will H Matthews
(74) Attorney, Agent, or Firm—Debra D. Condino; John Christopher James; Guy L. Cumberbatch

(57) ABSTRACT

A minimally invasive approach for surgery on portions of the heart and great vessels. A parasternal incision is made extending across a predetermined number of costal cartilages, e.g., a right parasternal incision extending from the lower edge of the second costal cartilage to the superior edge of the fifth costal cartilage. One or more costal cartilages, e.g., the third and fourth, are then excised to provide access to the portion of the heart or great vessels of interest, for example between a point approximately three centimeters above supra annular ridge and the mid ventricular cavity, and a desired procedure completed. A minimally invasive procedure for repair or replacement of the aortic valve is disclosed that includes making a transverse incision of so about 10 cm in length over the second or third intercostal space in the thorax of the patient, dividing the sternum transversely following the incision, retracting the transversely divided sternum, exposing the ascending aorta, and incising the ascending aorta to provide access to an area adjacent the aortic valve.

12 Claims, 17 Drawing Sheets

U.S. PATENT DOCUMENTS

| | | | |
|---|---|---|---|
| 5,304,183 A | 4/1994 | Gourlay et al. | |
| 5,312,344 A | 5/1994 | Grinfeld et al. | |
| 5,351,680 A | 10/1994 | Jung | |
| 5,370,685 A | 12/1994 | Stevens | |
| 5,374,272 A | 12/1994 | Arpa Paolo et al. | |
| 5,415,666 A | 5/1995 | Gourlay et al. | |
| 5,425,705 A | 6/1995 | Evard et al. | |
| 5,433,700 A | 7/1995 | Peters | |
| 5,452,733 A | 9/1995 | Sterman et al. | |
| 5,458,574 A | 10/1995 | Machold et al. | |
| 5,478,309 A | 12/1995 | Sweezer et al. | |
| 5,501,698 A | 3/1996 | Roth et al. | |
| 5,536,251 A | 7/1996 | Evard et al. | |
| 5,545,214 A | 8/1996 | Stevens | |
| 5,558,644 A | 9/1996 | Boyd et al. | |
| RE35,352 E | 10/1996 | Peters | |
| 5,569,274 A | 10/1996 | Rapacki et al. | |
| 5,571,215 A | 11/1996 | Sterman et al. | |
| 5,584,803 A | 12/1996 | Stevens et al. | |
| 5,588,949 A | 12/1996 | Taylor et al. | |
| 5,601,576 A | 2/1997 | Garrison | |
| 5,613,937 A | 3/1997 | Garrison et al. | |
| 5,618,306 A | 4/1997 | Roth et al. | |
| 5,618,307 A | 4/1997 | Donlon et al. | |
| 5,626,607 A | 5/1997 | Malecki et al. | |
| 5,752,526 A | 5/1998 | Cosgrove | |
| 5,875,782 A | 3/1999 | Ferrari et al. | |
| 6,182,664 B1 * | 2/2001 | Cosgrove | 128/898 |

FOREIGN PATENT DOCUMENTS

| | | |
|---|---|---|
| WO | WO 95/08364 | 3/1995 |
| WO | WO 95/10218 | 4/1995 |
| WO | WO 95/15192 | 6/1995 |
| WO | WO 95/15715 | 6/1995 |
| WO | WO 95/17919 | 7/1995 |
| WO | WO 95/21573 | 8/1995 |
| WO | WO 95/24940 | 9/1995 |
| WO | WO 96/00033 | 1/1996 |
| WO | WO 96/17644 | 6/1996 |
| WO | WO 96/21489 | 7/1996 |
| WO | WO 96/30073 | 10/1996 |
| WO | WO 96/32882 | 10/1996 |
| WO | WO 97/20506 | 6/1997 |

OTHER PUBLICATIONS

Journal of Cardiothoracic and Vascular Anesthesia—vol. 10, No. 4, Jun., 1996; pp. 631–635; "Anesthetic Considerations for Patients Undergoing Minimally Invasive Coronary Artery Bypass Surgery: Mini–Sternotomy and Mini–Thoractomy Approaches", J. M. Gayes MD, et al.

The Society of Thoracic Surgeons, 1996, "Mini–Sternotomy for Coronary Artery By Pass Grafting"; K. V. Arom, MD. et al.

The Society of Thoracic Surgeons, 1996; "Minimally Invasive Coronary Artery Bypass Grafting"; T.E. Acuff MD, et al.

Thorac. Cardiovase Surgeon 32 (1984) 331–333 Revival of Right Thoracotomy to Approach Atrio–ventricular Valves in Reoperations, E.Berreklouw and O. Alfieri.

* cited by examiner

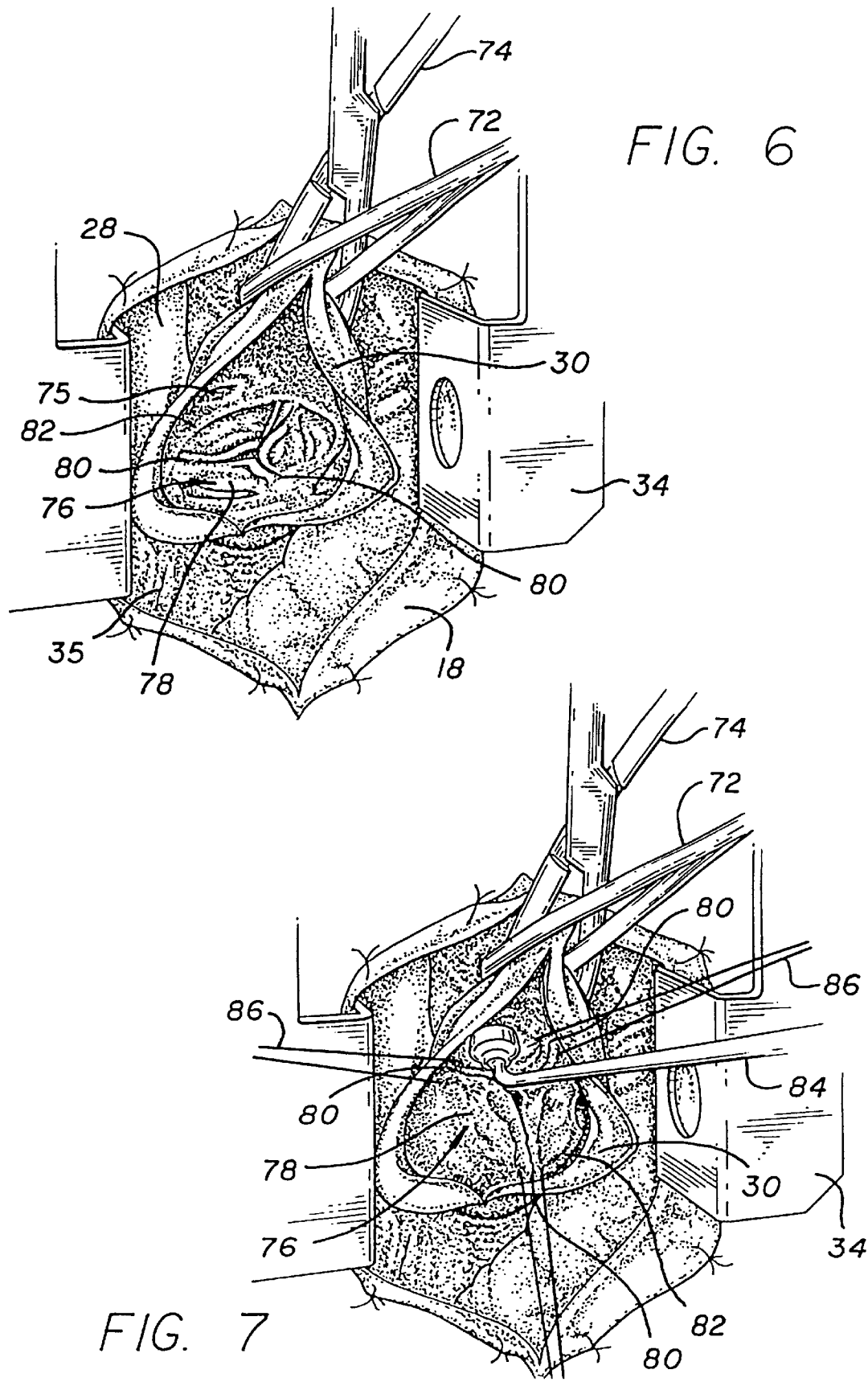

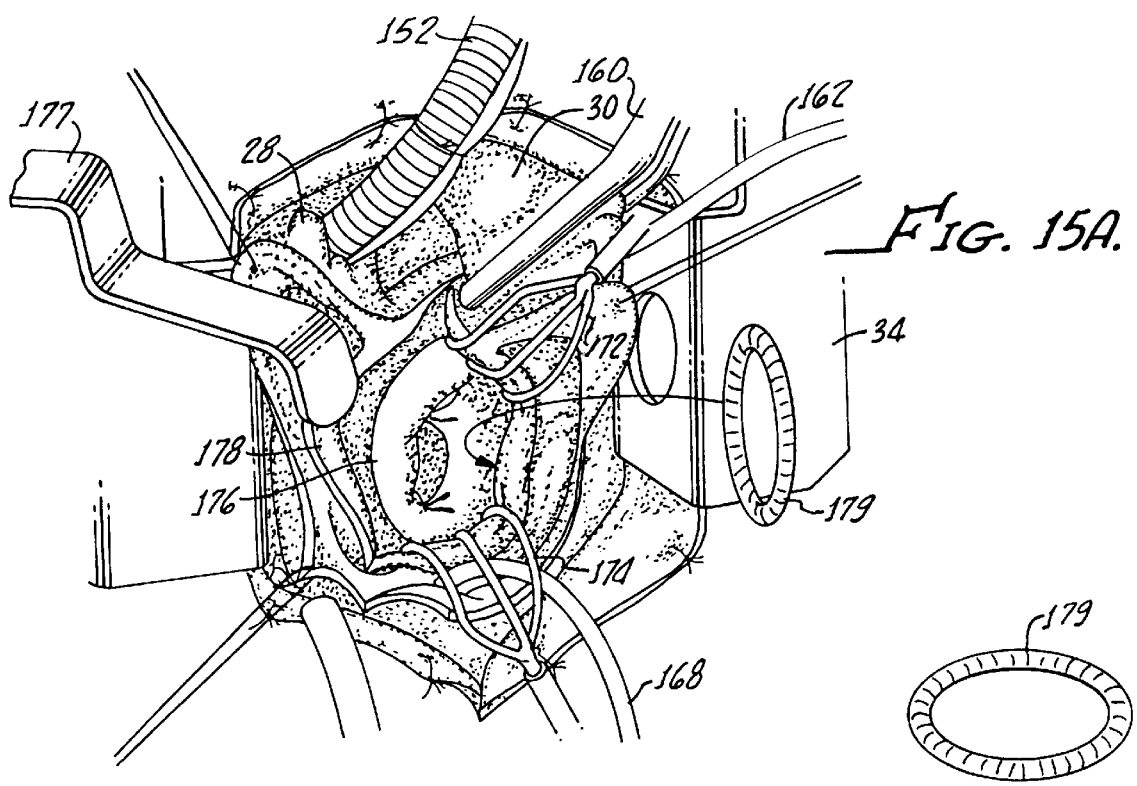
FIG. 15A.
FIG. 15B
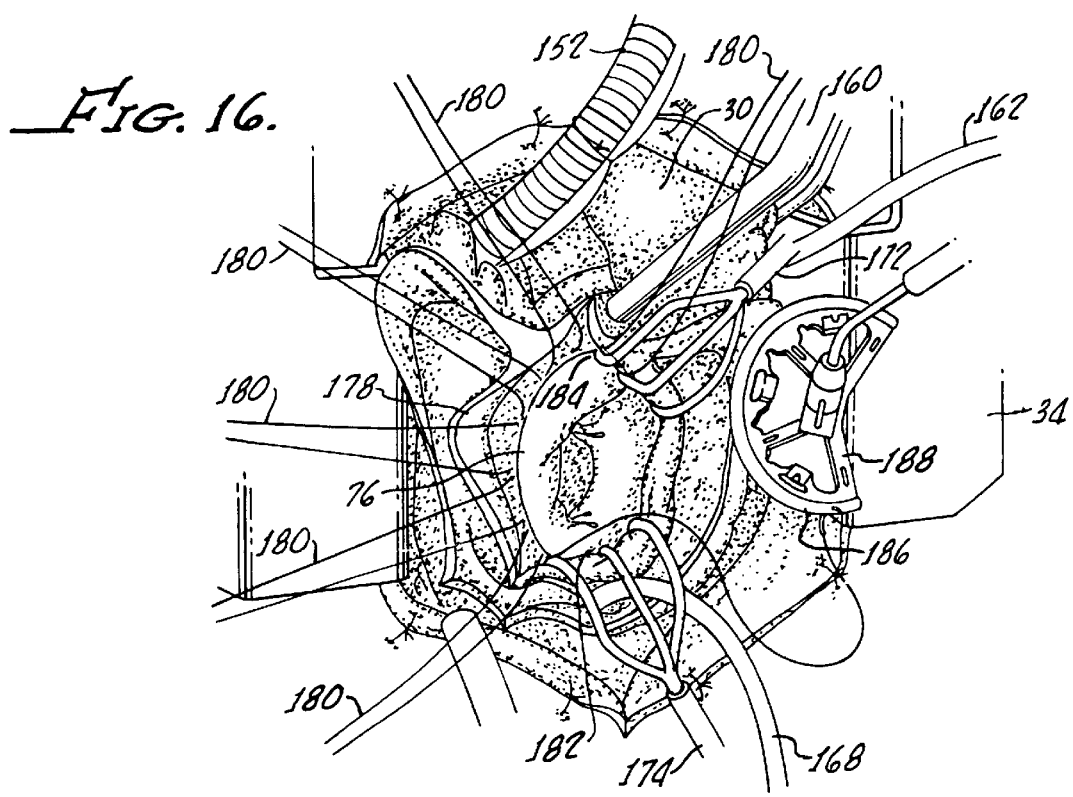
FIG. 16.

_FIG. 25._
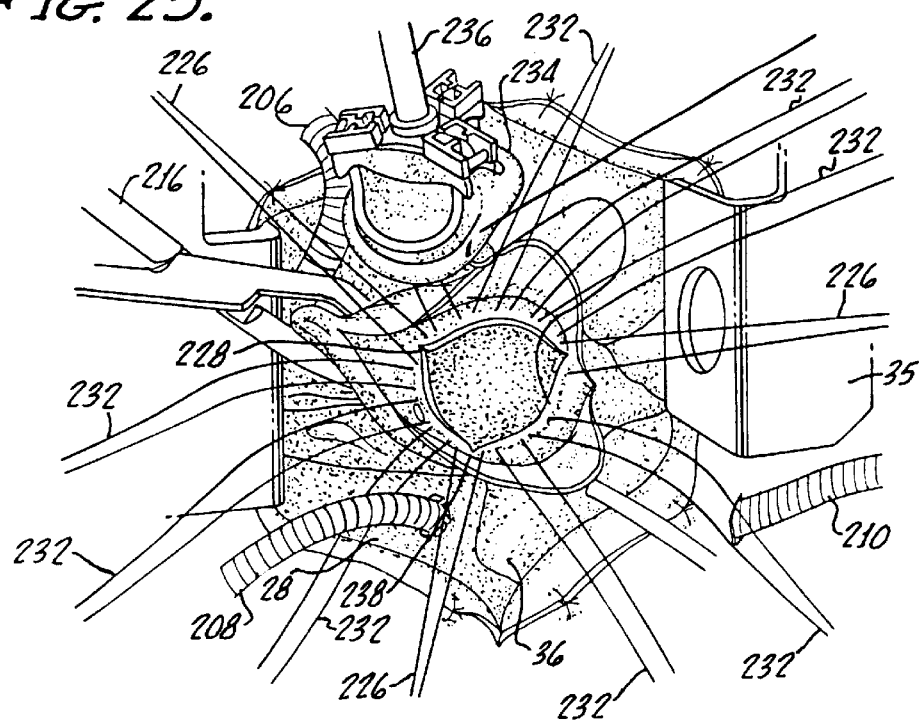
_FIG. 26._
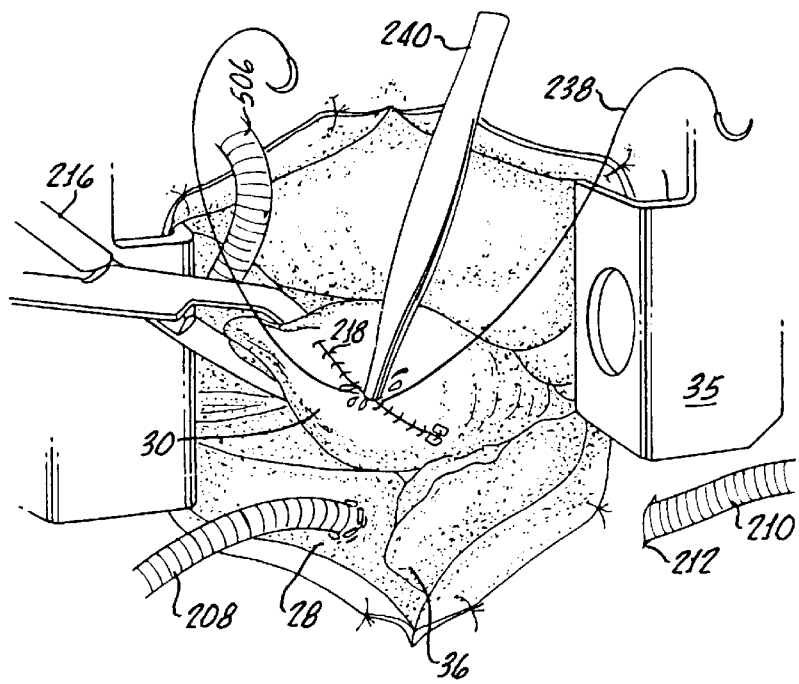

MINIMALLY INVASIVE CARDIAC SURGERY PROCEDURE

RELATED APPLICATIONS

The present application is a continuation of U.S. application Ser. No. 08/801,494, filed Feb. 18, 1997, now U.S. Pat. No. 6,182,664 which is a continuation-in-part of U.S. application Ser. No. 08/603,313, filed Feb. 19, 1996, now issued as U.S. Pat. No. 5,752,526.

BACKGROUND OF THE INVENTION

1. Field of the Invention

The present invention relates to surgical procedures and, more specifically, to minimally invasive procedures for mitral and aortic valve repair or replacement surgeries including making small access incisions in the sternal area.

2. Description of the Related Art

Various types of surgical procedures are performed on the heart and the great vessels. Many of such procedures, particularly those involving the aorta, and aortic valve employ a gross thoracotomy, e.g., a median sternotomy, in order to gain access to the involved portion of the heart or vessel. In other words, the procedures entail splitting open the patient's chest. Such procedures cause significant trauma to the patient, and recovery time.

An example is the conventional procedure for aortic valve surgery. The patient is anesthetized, and the skin is incised from the top of the sternum to a point located a predetermined distance, e.g., approximately two inches, below the bottom of the sternum. The sternum is then split longitudinally, using a saw or other cutting implement. A spreader is placed within the chest cavity and the opposing halves of the rib cage spread apart to expose the thoracic cavity. The tissues around the heart are divided, opening the pericardial sack. A cardiopulmonary bypass is initiated through direct aortic and right atrial cannulation (that is, circulation to a heart-lung machine is established through an arterial-returning catheter disposed in the aorta and a venous drainage catheter in the right atrium); the aorta is clamped (typically between the brachycephalic artery and the coronary ostia) to exclude the heart from the circulation. The cardiac function is then arrested, i.e., the heart is stopped by infusion of a cardioplegia fluid, such as a cold potassium solution. The aorta is then opened. The valve is then repaired, or if to be replaced, excised and a replacement valve sewn in. Any air that may have accumulated in the heart during the procedure is then removed from the heart and the aorta closed with sutures. The clamp is then removed, patient weaned from the heart-lung machine, tubes removed from the aorta, the sternum wired back together and the skin closed with sutures.

Such procedures are particularly traumatic. Incisional pain tends to require significant postoperative analgesia and postoperative discomfort tends to result in significant patient morbidity and lengthy hospital stays. In addition, because the pericardial sack is opened underlying the sternum, after the procedure the heart has a tendency to become adherent to the sternum. This can be problematical in the event of subsequent procedures.

The desirability of avoiding the use of median sternotomy, and other gross thoracotomy procedures, in connection with surgery on the heart and the great vessels has been recognized. For example, techniques have been proposed in which a scope is inserted through a percutaneous intercostal penetration in the patient's chest (an incision between the ribs) to observe internal procedures performed by instruments introduced into the chest with the scope, or through cannula disposed in other intercostal spaces, i.e., between two adjacent ribs. Such techniques and instruments for performing such techniques within the heart and great vessels is described in International Publication WO 95/15715 by Sterman, et al., published Jun. 15, 1995. However, such techniques require special instrumentation and special skills to perform, and may extend the time the heart is arrested and the duration of the procedure.

SUMMARY OF THE INVENTION

The present invention provides a minimally invasive approach for mitral or aortic valve surgeries. In accordance with one aspect of the present invention, a parasternal incision is made extending across a predetermined number of costal cartilages, e.g., a right parasternal incision extending from the lower edge of the second costal cartilage to the superior edge of the fifth costal cartilage. One or more costal cartilages, e.g., the third and fourth, are then excised to provide access to the mitral valve, and a desired mitral valve repair or replacement procedure completed. In accordance with another aspect of the invention an approximately 10 cm incision is made transverse to the sternum over the second intercostal space. The sternum is then divided thereby exposing access to the ascending aorta, and a desired aortic valve replacement procedure completed.

A minimally invasive procedure for repair or replacement of the aortic valve is disclosed that includes making a transverse incision of about 10 cm in length over the second or third intercostal space in the thorax of the patient, dividing the sternum transversely following the incision, retracting the transversely divided sternum, exposing the ascending aorta, and incising the ascending aorta to provide access to an area adjacent the aortic valve.

BRIEF DESCRIPTION OF THE DRAWINGS

A preferred exemplary embodiment of the present invention will hereinafter be described with reference to the appended drawing, wherein like denominations indicate like elements, and;

FIG. 6 is a pictorial illustration depicting the right parasternal incision of FIG. 1 after the aorta is opened to expose the aortic valve;

FIG. 7 is a pictorial illustration of injection of cardioplegia into the coronary ostia;

FIG. 15A and 15B are a pictorial illustration depicting alternative ways of exposing the surgical field of FIG. 15;

FIG. 16 is a pictorial illustration of the performance of an annuloplasty in the surgical field of FIG. 15;

FIG. 25 is a pictorial illustration of the replacement of an aortic valve in the surgical field of FIG. 22;

FIG. 26 is a pictorial illustration of the closure of the aorta in the surgical field of FIG. 22; and, FIG. 27 is a pictorial illustration of the surgical field of FIG. 22 after completion of the surgery.

DESCRIPTION OF THE EXEMPLARY EMBODIMENTS

Figure 1:
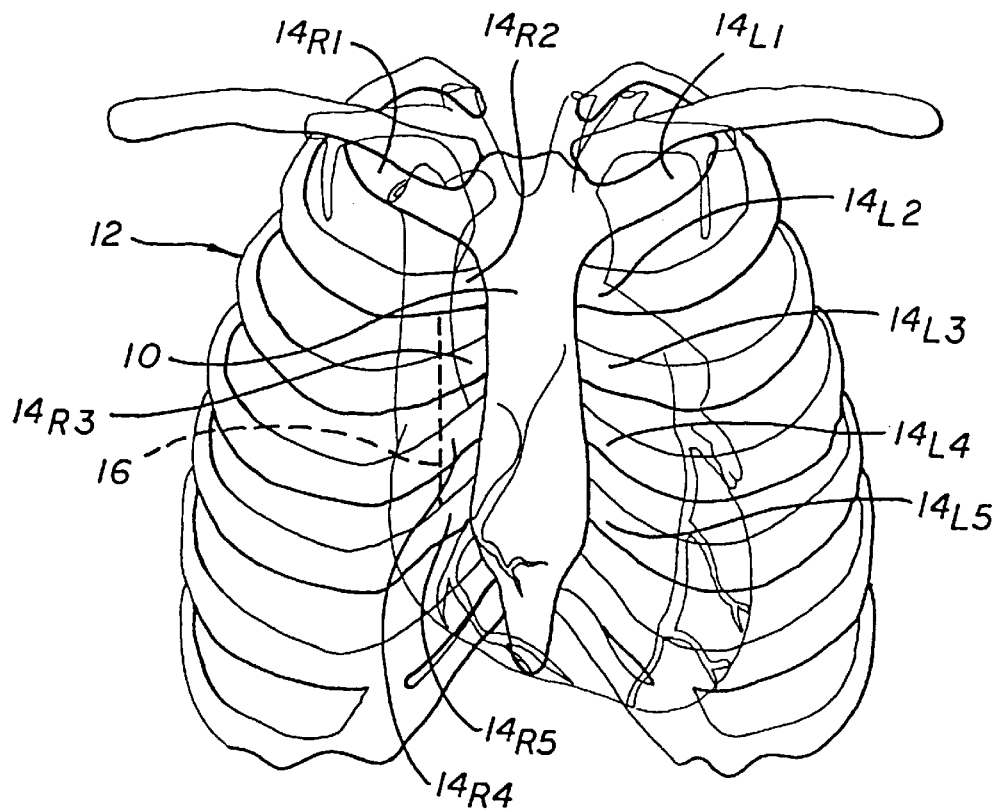
FIGS. 1 and 1A are schematic illustrations depicting a human chest and the disposition of a right parasternal incision in connection with an aortic surgery procedure in accordance with the present invention.

Referring now to FIG. 1, in a typical human, a sternum 10, a planary bone structure centrally disposed in the chest, is connected to a plurality of ribs 12 by respective costal cartilages $14_{R1}$, $14_{R2}$, $14_{R3}$, $14_{R4}$, $14_{R5}$, and $14_{L1}$, $14_{L2}$, $14_{L3}$, $14_{L4}$, $14_{L5}$. The heart and great vessels are located within a tissue sack (pericardium), located beneath the sternum, extending laterally under the costal cartilages and ribs, with the aorta disposed in part underlying the second and third right costal cartilages $14_{R2}$ and $14_{R3}$ and a portion of the right coronary artery located generally underlying the vicinity of the fourth and fifth right costal cartilages $14_{R4}$ and $14_{R5}$.

Figure 1A:
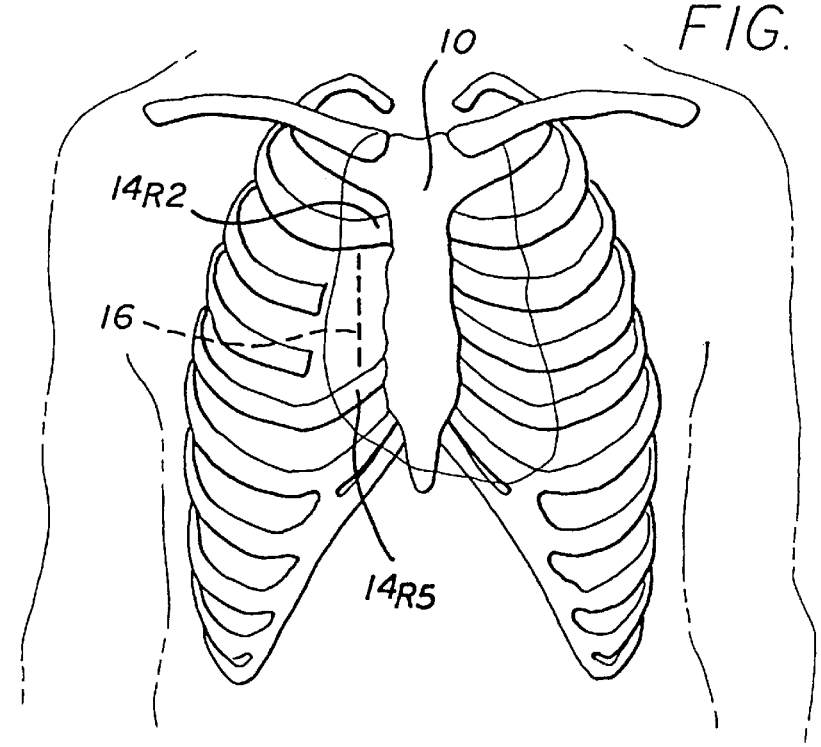

In accordance with one aspect of the present invention, it has been determined that a surgery on portions of the heart and great vessels located between a point approximately three centimeters above the supra annular ridge and the mid-ventricular cavity, can be effected with minimal invasion, without a median sternotomy, or other gross thoracotomy, by, as illustrated in FIG. 1A, making a relatively short parasternal incision 16 extending across a predetermined number of costal cartilage, e.g., a right parasternal incision extending from the lower edge of the second costal cartilage $14_{R2}$ to the superior edge of the fifth costal cartilage $14_{R5}$ and removing one or more costal cartilages, e.g., the third and fourth costal cartilages, $14_{R3}$ and $14_{R4}$. It has been determined that over a period of time the chest wall in the area of the resected cartilages becomes stable secondary to scarring of the remaining tissue. In effect, scar tissue resulting from the procedure functionally replaces the excised cartilage, providing a relatively rigid chest wall.

This procedure can be readily employed to perform operations on structures located on portions of the heart and great vessels located between a point approximately three centimeters above the supra annular ridge and the mid-ventricular cavity. As will be more fully described, the procedure is of particular utility with respect to surgery to repair or replace the aortic valve. Further, in some instances, the minimally invasive approach of the present invention can be employed to effect a variety of other operations, such as, for example, septal myectomy (excision of a portion of the muscle just below the aortic valve to correct an obstruction to the outflow of the heart); closure of a ventricular septal defect (e.g., a congenital hole in the heart); and correction of aneurysms.

The minimally invasive approach of the present invention is particularly advantageous as compared to a median sternotomy. In addition to decreased trauma to the patient, and the attendant benefits, the minimally invasive technique provides additional advantages in the event of repeat surgery. Since the pericardial sack underlying the sternum is opened under the sternum in a median sternotomy, after the procedure the heart has a tendency to adhere to the sternum. This can be problematical in the event of subsequent procedure; there is a risk of cutting into the heart when sawing through the sternum during the subsequent operation. In contradistinction, in the procedure according to the present invention, the pericardium underlying the sternum remains intact, normal tissue is retained between the sternum and the heart and there is no risk of the heart adhering to the sternum. A series of operations are relatively common in connection with correction of congenital heart disease.

As noted above, the minimally invasive approach of the present invention is of particular utility with respect to surgery to repair or replace the aortic valve. Specifically, in the context of exemplary surgery to replace an aortic valve, the patient is anesthetized and intubated, and placed supine on the operating room table. Preferably, defibrillator pads are placed on the patient's back and anterior left chest, and a transesophageal echocardiography probe is placed to access the etiology of the aortic valve disease and to assist in removing air from the heart after completion of the operation.

Figure 2:
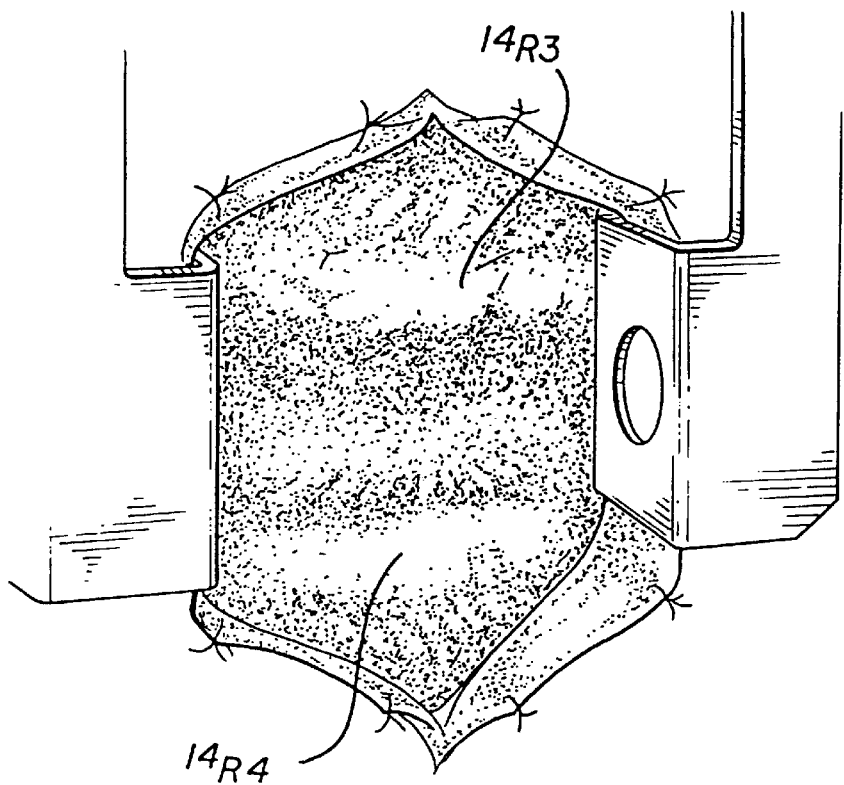
FIG. 2 is a pictorial illustration depicting the right parasternal with incision of FIG. 1 showing respective costal cartilages.
Figure 3:
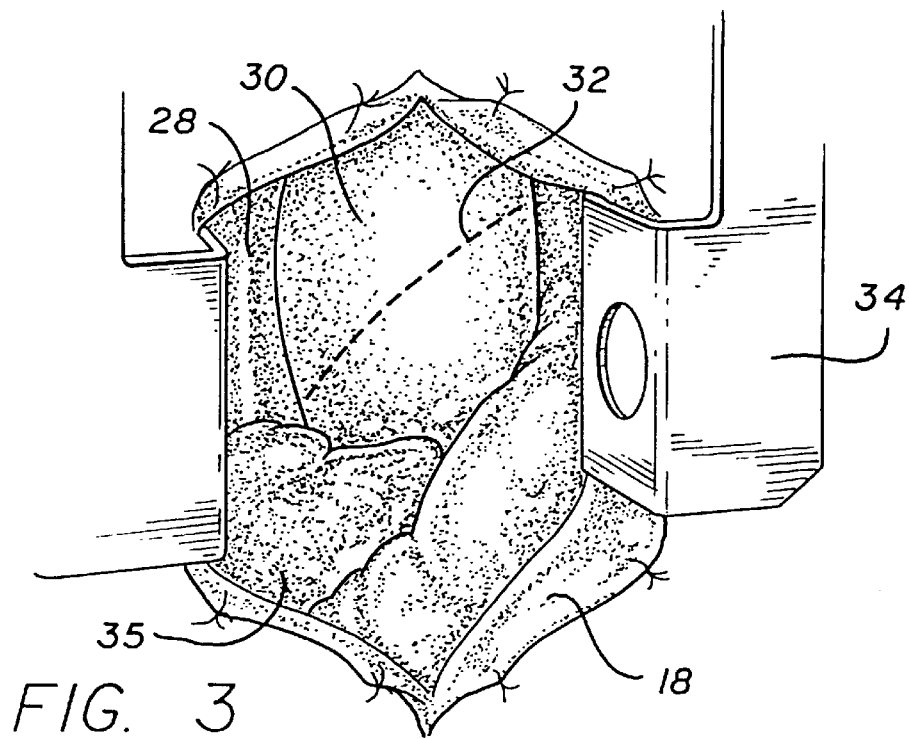
FIG. 3 is a pictorial illustration depicting the right parasternal incision of FIG. 1 after respective costal cartilage units are excised and the incision retracted.

Referring to FIGS. 1 and 1A, a right parasternal incision is made extending from the lower edge of the second costal cartilage $14_{R2}$ to the superior edge of the fifth costal cartilage. The pectoral major muscle is divided, exposing the second, third, and fourth intercostal spaces, and the third and fourth costal cartilages $14_{R3}$ and $14_{R4}$ as shown in FIG. 2. The third and fourth costal cartilages $14_{R3}$ and $14_{R4}$ are totally excised (FIG. 1A). The right internal thoracic artery is ligated just below the second costal cartilage $14_{R2}$ and just above the fifth costal cartilage $14_{R5}$. Intercostal muscles and pleura are incised lateral to the edge of the sternum, entering the right pleural cavity. As shown in FIG. 3, the pericardium 18 is then incised, exposing the ascending aorta 30, and is stitched back. The incision is held open using a conventional chest retractor 34.

Figure 4:
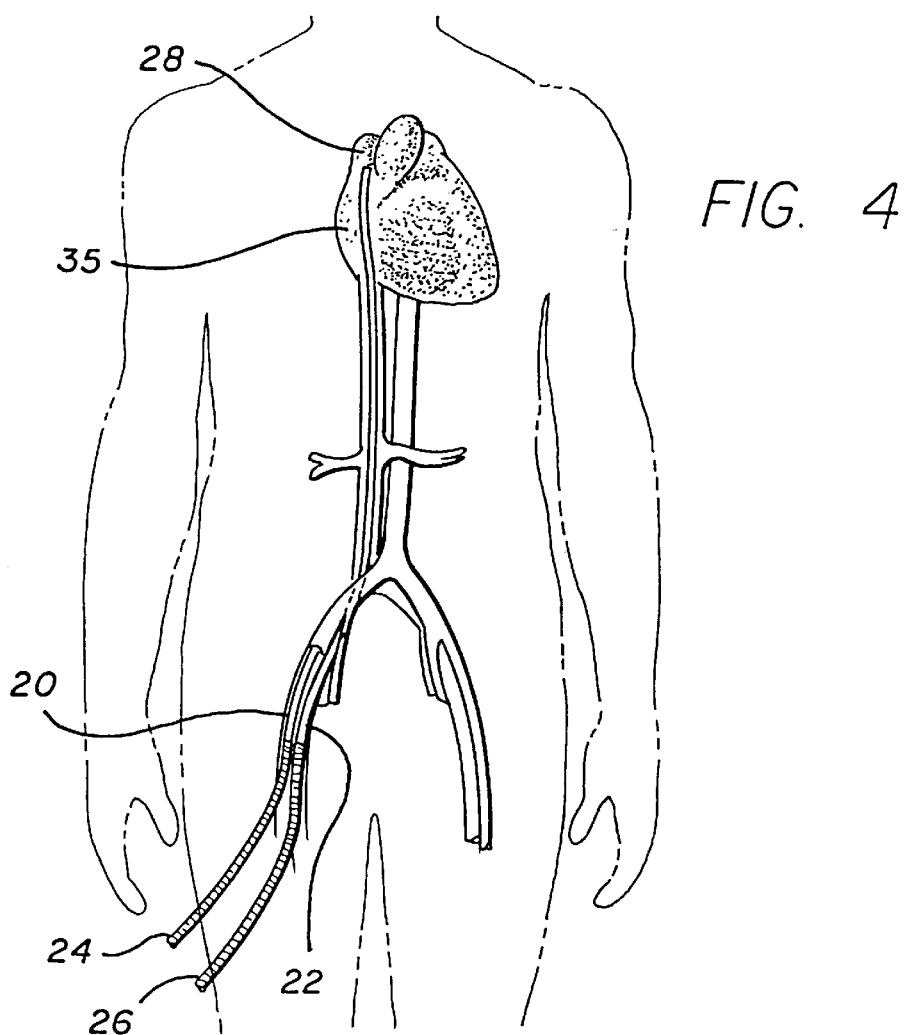
FIG. 4 is a schematic illustration depicting the disposition of respective by-pass cannula employed in connection with an aortic surgery procedure in accordance with the present invention.
Figure 5:
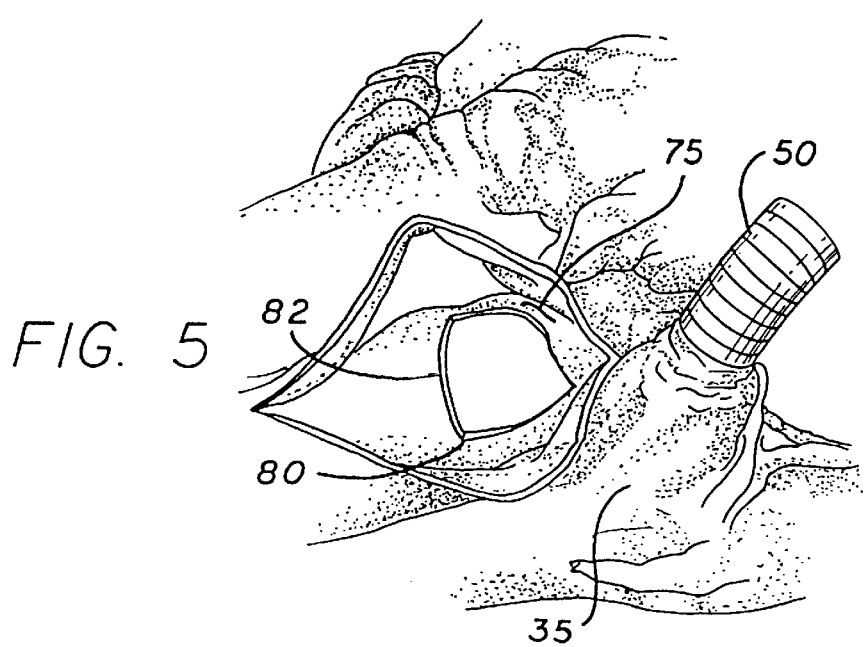
FIG. 5 is a schematic illustration depicting an alternative disposition of respective by-pass cannula employed in connection with an aortic surgery procedure in accordance with the present invention.

A cardiopulmonary by-pass is then established. Referring now to FIG. 4, a common femoral artery 20 and vein 22 are exposed and, after infusion of an anti-coagulant, e.g., heparinization, are cannulated. Catheters 24 and 26 are placed in femoral artery 20 and in femoral vein 22, respectively. Adequate venous drainage may be obtained by utilizing a long venous cannula 26 disposed so that the tip of the cannula passes through the right atrium 35 and preferably into the superior vena cava 28 (FIG. 3). Alternatively, as illustrated in FIG. 5, venous return can be effected by introducing an appropriate catheter 50 into the right atrial appendage 35. (The anatomy depicted in FIG. 5 illustrates the results of additional steps in the procedure, as will be explained). Catheters 24 and 26 direct the blood to a conventional heart-lung machine (not shown) which oxygenates the blood and pumps it back under pressure to the patient.

Referring to FIG. 6, after catheters 24 and 26 are placed, the heart is excluded from circulation: aorta 30 is suitably encircled with umbilical tape 72 and the ascending aorta 30 cross clamped with a right angle clamp 74.

With continued reference to FIG. 6, the aorta is then incised (along line 32, FIG. 3) to expose the coronary ostia 75 and the aortic valve 76. Aortic valve 76 includes a plurality, typically three, of leaflets (valve cusps) 78, joined at respective commissures 80, and surrounded by a relatively fibrous aortic annulus 82.

Cardiac function is arrested, by e.g., by administering cardioplegia into the ascending aorta. Referring now to FIG. 7, after performing the aortatomy, a suitable cardioplegia is introduced into the left coronary artery. Preferably, a suitable cardioplegia fluid, such as a cold potassium solution is infused through a catheter 94 inserted in coronary ostia 75. Sutures 86 are then suitably placed just above each commissure 80, and clamped under tension to a drape (not shown) surrounding the operating site. This elevates the aortic root (e.g., aortic annulus 82) into the operative field.

Figure 8:
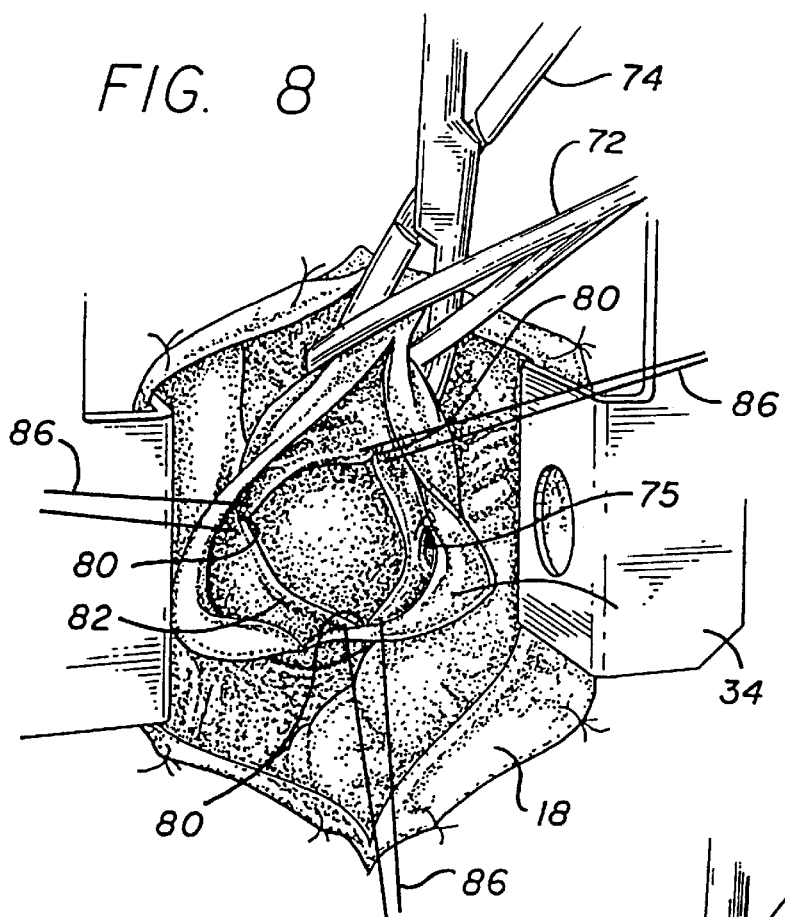
FIG. 8 is a pictorial illustration depicting the right parasternal incision of FIG. 1 after the aortic valve is removed, with traction sutures placed at the commissures.
Figure 9:
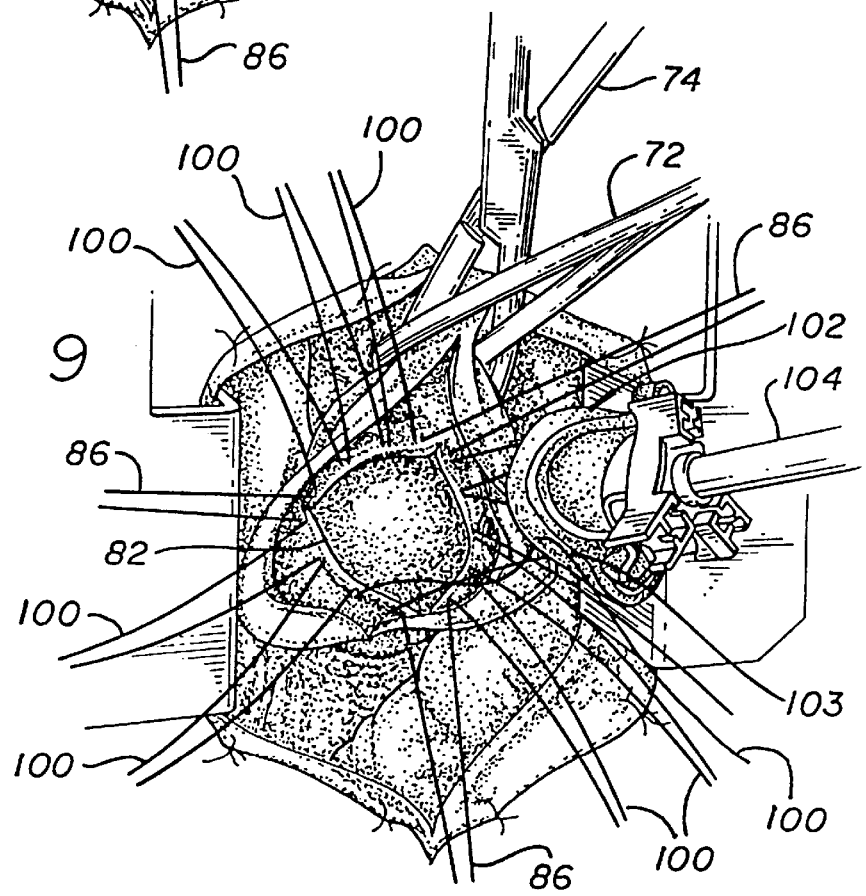
FIG. 9 is a pictorial illustration depicting insertion of an aortic valve prosthesis.

Aortic valve 76 is then either repaired or replaced. For example, referring to FIGS. 8 and 9, where a valve replacement is effected, valve cusps 78 are excised, leaving aortic annulus 82 (FIG. 8; see also FIG. 5). A multiplicity of sutures 100 are then placed through aortic annulus 82 about the periphery of the void left by excision of the valve cusps 78 (FIG. 9). Sutures 100 are then employed to secure a suitable replacement valve 102. Replacement valve 102 may be, e.g., a bioprosthesis (cusps formed from animal tissue coupled to a suitable peripheral sewing ring, formed of e.g., polyester velour), a mechanical prosthesis (cusps formed from e.g., pyrolytic carbon with a suitable peripheral sewing ring 103, formed of e.g., polyester velour), or a homograft (e.g., formed from human tissue which was frozen in liquid nitrogen, then thawed). Attachment of the bioprosthesis and mechanical prosthesis replacement valves are suitably facilitated using a conventional insertion tool 104. Replacement valve 102 is typically attached to aortic annulus 82 by passing sutures 100 through sewing ring 103 of the replacement. A vent is intermittently placed into the left ventricle through the aortic annulus as needed.

Figure 10:
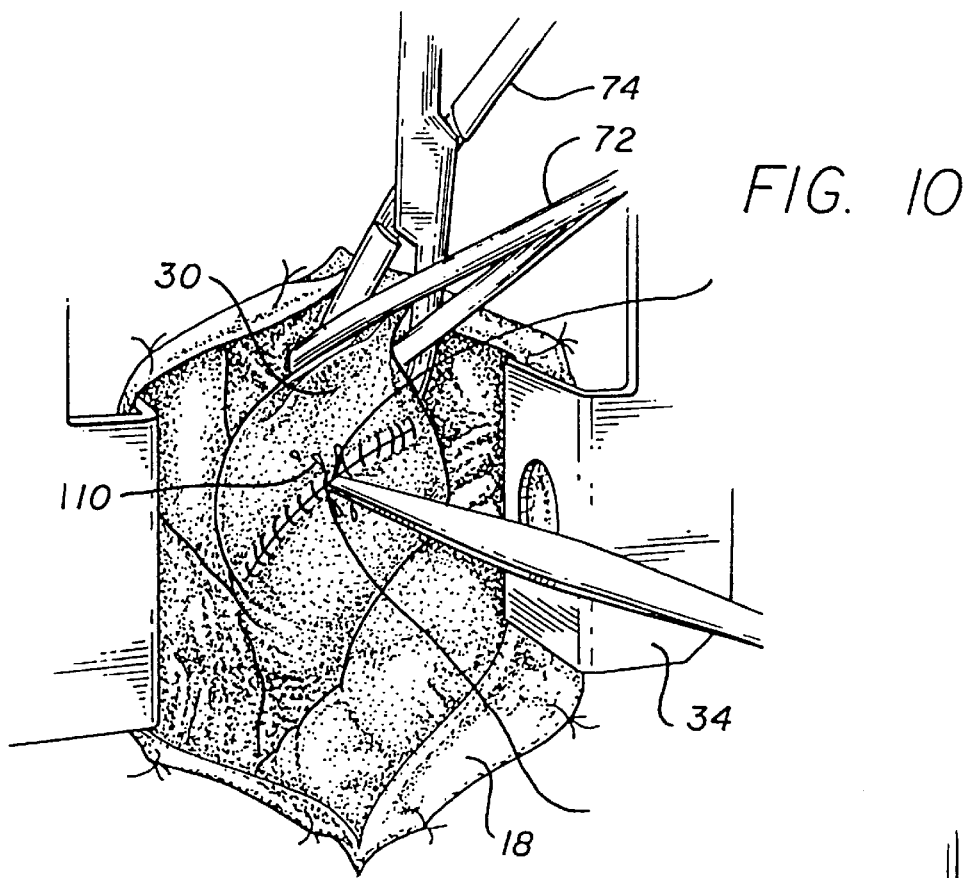
FIG. 10 is a pictorial illustration depicting closure of the aorta.

At the completion of the repair or replacement, the aortatomy is closed with sutures 100, as shown in FIG. 10. Air is then removed from the heart through the aorta with the assistance of the transesophageal echocardiography probe; all air bubbles are preferably removed from the heart by removing clamp 74 to restore blood flow, and inflating the lungs, until blood flows through sutures 110, then tightening the sutures.

Figure 11:
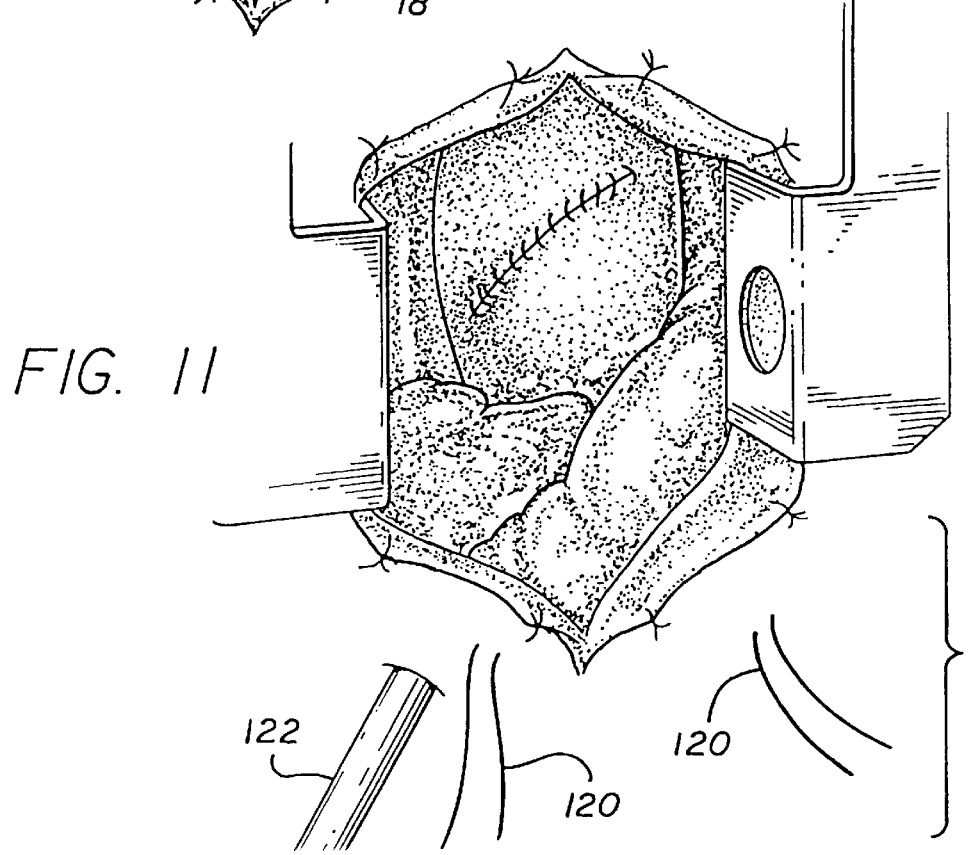
FIG. 11 is a pictorial illustration depicting the disposition of temporary pacer leads and a drainage tube.

Referring to FIG. 11, temporary pacemaker leads 120, 122 are placed on the atrium and on the ventricle to facilitate temporary pacing should it be necessary. The patient is weaned from cardiopulmonary bypass, the femoral vessels are decannulated and repaired, conventional right-sided pleural chest tubes 122 are placed, and the femoral and right parasternal incisions are closed, suitably by reapproximating the muscle, subcutaneous tissue and skin, in layers.

In another aspect of the present invention, a similar incision as that described above with reference to FIGS. 1, 1A and 2, can be used in performing surgery to repair or replace a mitral valve. More specifically, referring to FIGS. 1A and 2, a parasternal incision approximately 10 cm in length is made over the third and fourth intercostal cartilages $14_{R3}$ and $14_{R4}$. The pectoralis major muscle is then divided longitudinally, exposing the third and fourth cartilages $14_{R3}$, $14_{R4}$. The cartilages $14_{R3}$, $14_{R4}$ are completely resected and the internal thoracic artery (not shown) is then ligated and divided. The pericardium 18 is opened and suspended under tension to the drapes of the patient.

Figure 12:
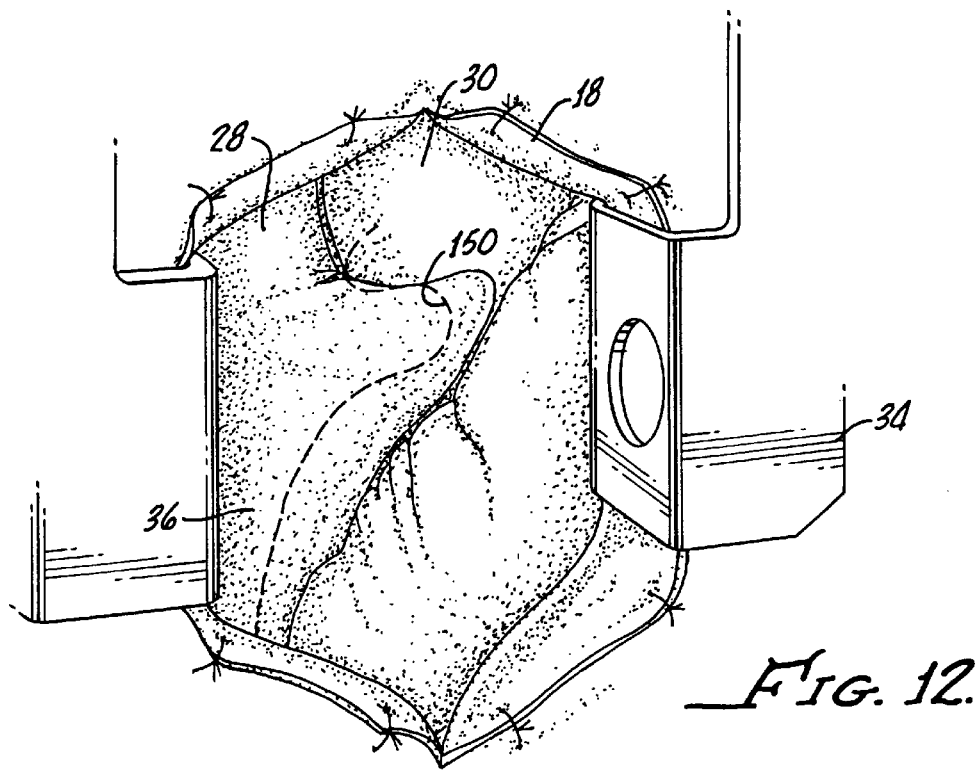
FIG. 12 is a pictorial illustration depicting a right parasternal incision after respective costal cartilage units are excised and the incision retracted.

Referring to FIG. 12, the resulting wound provides access into the chest cavity and particularly exposes the first portion of the ascending aorta 30, the superior vena cava 28 and the right atrium 36. The wound also provides access for making a planned incision 150 into the right atrium 36.

Figure 13:
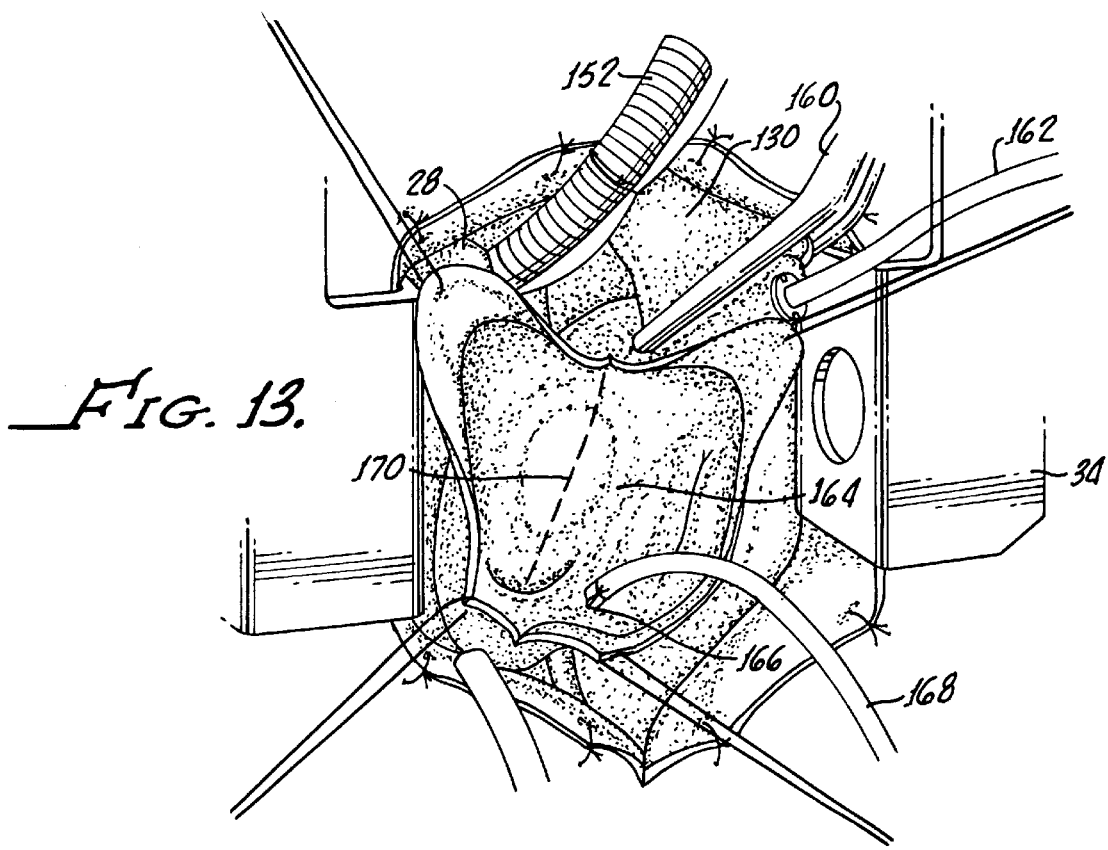
FIG. 13 is a pictorial illustration depicting the surgery field of FIG. 12 after an incision of the right atrium.
Figure 23:
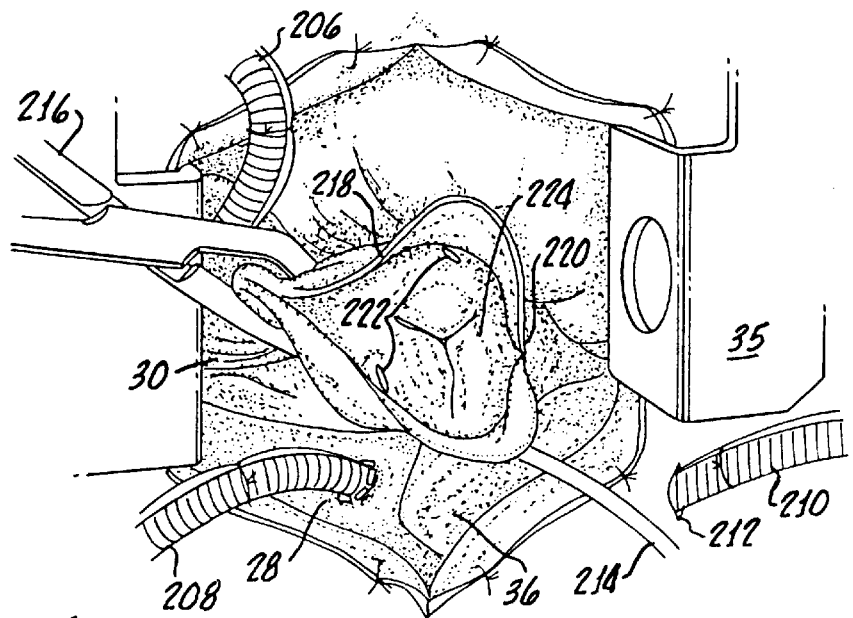
FIG. 23 is a pictorial illustration of an incised aorta in the surgical field of FIG. 22.

Referring to FIG. 13, prior to making the incision 150 into the right atrium 36, the patient must be cannulated so that the heart may be bypassed from blood flow during the surgery on the heart. In that connection, a first cannula 152 is inserted directly into the superior vena cava 28. A second cannula 210 (FIG. 23) may be inserted into the inferior vena cava, either via the right atrium 36 or via a venous cannula introduced through a femoral vein as known in the art. Arterial return is established by a third cannula 206 which may be inserted either directly into the ascending aorta 30 as shown in FIG. 23 or through a femoral artery as depicted in FIG. 4.

The cannulation configuration for heart bypass will be dictated in large part by patient anatomy and physiology particularly with regard to the size and placement of the heart within the chest cavity, and the resulting effect of that anatomy and physiology on the incision exposure. It is desirable, however, to achieve as much of the bypass cannulation as possible through the primary incision so as to reduce the number of incisions otherwise made in the patient for peripheral cannulation as shown in FIG. 14.

Figure 14:
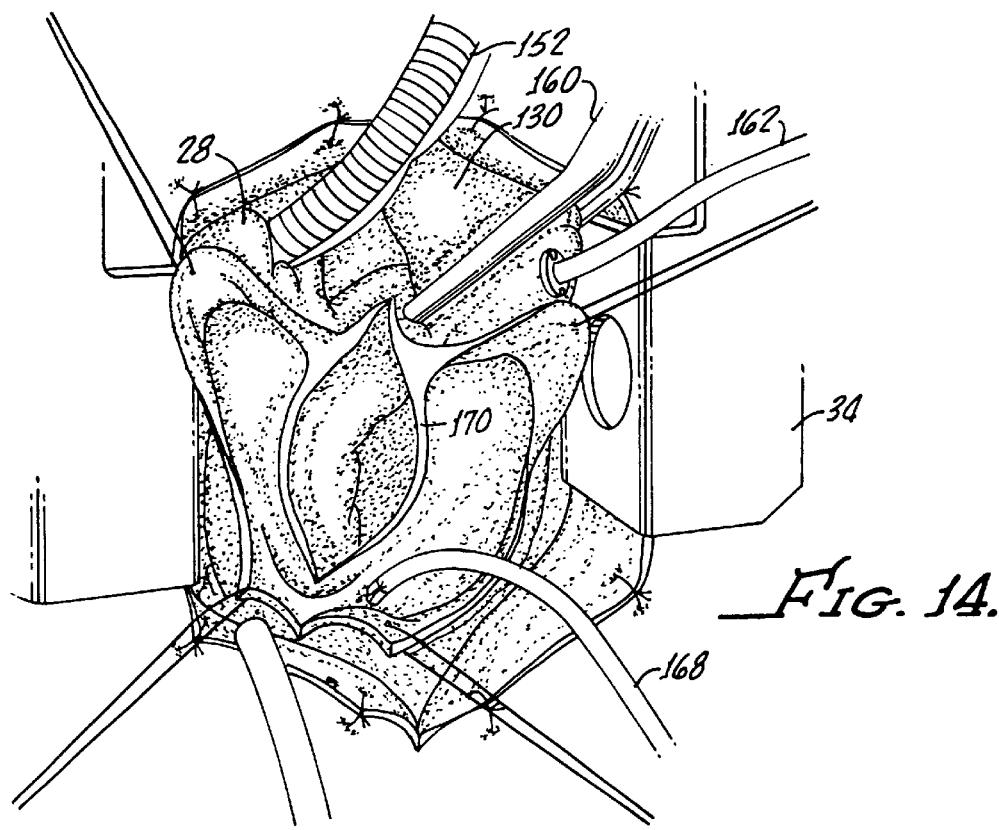
FIG. 14 is a pictorial illustration depicting the surgical field of FIG. 12 after an incision of the inter-atrial wall.

Once cannulation is complete, a cross clamp 160 is applied to the ascending aorta 30 as shown in FIG. 14 to occlude blood flow. Antegrade cardioplegia is then applied directly into the ascending aorta proximal of the clamp via a cardioplegia catheter 162. Bypass is established and then the heart progressively diminishes its beating activity until it ceases beating altogether.

Figure 13A:
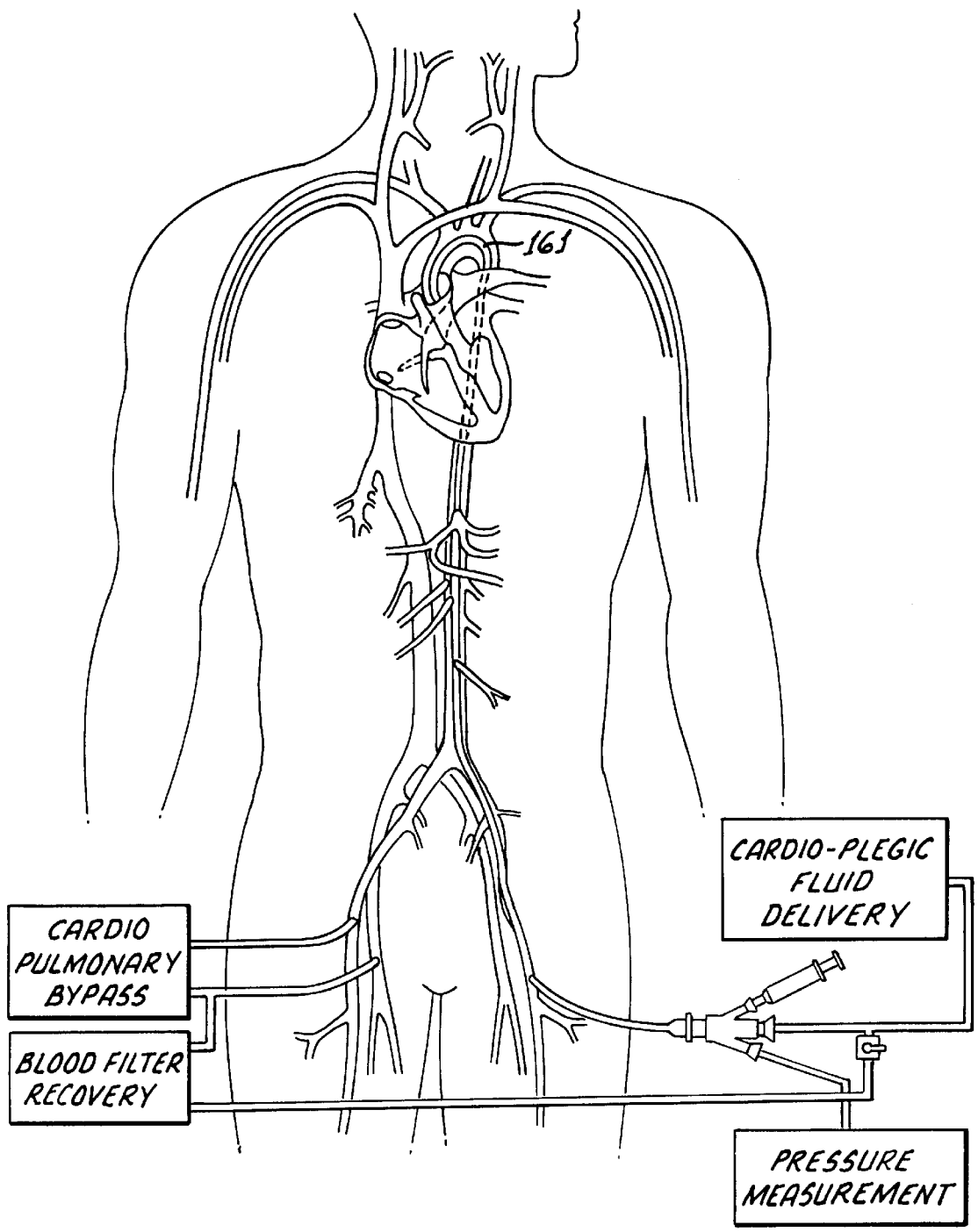
FIG. 13A is a pictorial illustration depicting an alternative way of occluding the aorta.
Figure 13B:
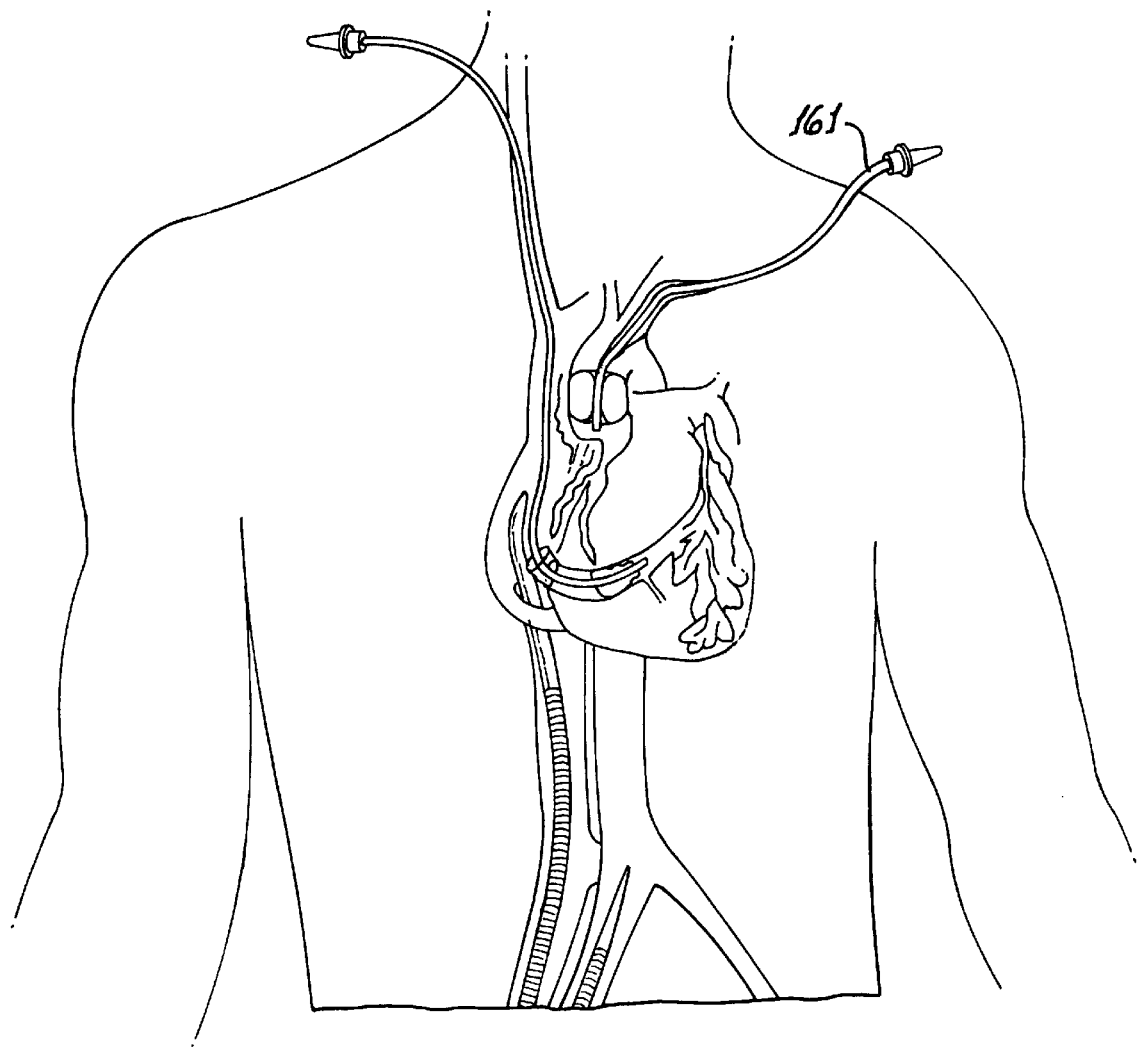
FIG. 13B is a pictorial illustration depicting an alternative way of occluding the aorta.

Referring to FIGS. 13A and 13B, it is appreciated that an aortic occlusion balloon could alternatively be used to block the ascending aorta for establishing bypass. In particular, an aortic occlusion balloon catheter 161 could be introduced either through the femoral artery, as shown in FIG. 13A, the sub-clavian artery as shown in FIG. 13B or other vessel in a manner to position the balloon between the coronary ostia and the brachycephalic artery of the ascending aorta. Occlusion is achieved by inflating the balloon so that the balloon contacts the internal wall of the aorta and thereby blocks blood flow in the aorta. Cardioplegia may then be introduced into the coronary ostia either directly through the aorta as previously described or through a cardioplegia lumen extending to a distal end of the aortic balloon catheter.

With further reference to FIG. 13B, it is appreciated that under certain circumstances, in accordance with the method of the present invention can be performed using a retrograde application of cardioplegia. The retrograde cardioplegia catheter placed in the coronary ostia through the jugular vein and the right atrium. It is further appreciated that the type of cardioplegia used, whether introduced antegrade or retrograde, will often be dictated by the anatomy and physiology of the patient or by the preference of the physician.

Once bypass is established, the incision 150 into the right atrium 36 is made and the tissue draped back to expose the coronary sinus 166 and intra-arterial septum 164 (FIG. 13). Additional cardioplegia is introduced, as necessary, in a retrograde fashion into the coronary sinus 166 with a retrograde cardioplegia catheter 168. The retrograde cardioplegia catheter 168 can be either a conventional retrograde catheter or an occluding balloon catheter to ensure proper introduction of the cardioplegia without leakage. The stage is then set to cut the intra-atrial septum 164 along an incision line 166 and thereby expose the dome of the left atrium.

Figure 15:
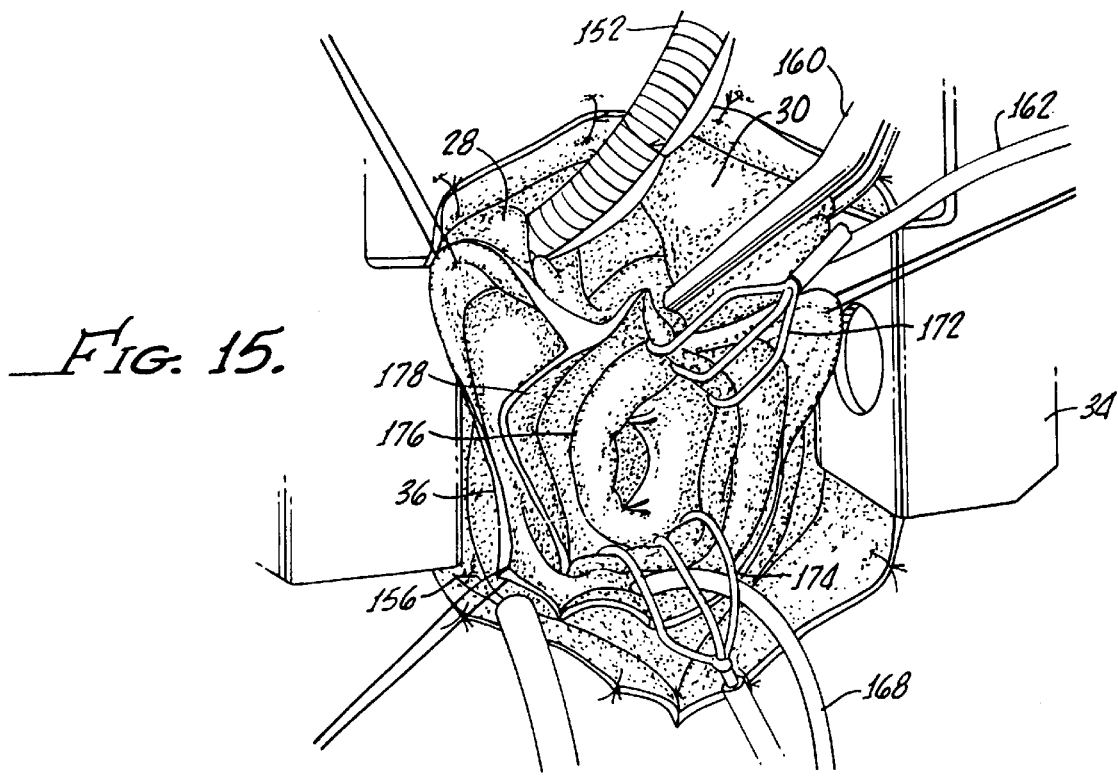
FIG. 15 is a pictorial illustration depicting the surgical field of FIG. 12 after the tissue has been retracted.

Referring to FIGS. 14 and 15, the incision 170 is made in the intra-atrial septum 164 starting at the foramen ovale and extending inferiorly and superiorly into the dome of the left atrium. Hand-held refractors 172, 174 are then inserted into the superior and inferior portions of the left atrium, respectively, and used to pull the atrial tissue back and expose the mitral valve 176. Additionally, downward traction may be applied on the posterior lateral left atrial wall 178 to provide better exposure to the mitral valve 176. Referring to FIGS. 15A and 15B, a deformable retractor 177, which may be manipulated into a shape that grasps the tissue but does not obstruct the surgical field, may be used to provide the downward traction on the posterior lateral left atrial wall 178. In addition, to further expose the surgical field, a flexible and resilient ring member 179 may be inserted into the field between the valve 176 and the left atrial wall. After the ring member is inserted, the ring 179 expands to facilitate lifting the tissue away from the valve area requiring surgery. The mitral valve 176 being fully exposed after achieving the above-described configuration, repair or replacement of the valve 176 may then be achieved in the conventional manner. By way of example only, the procedure for completing the surgical method after repair of a mitral valve is hereinafter described.

Referring to FIG. 16, after repair of the mitral valve 176, an annuloplasty is performed. In particular, horizontal mattress sutures 180 of multi-filament 2-0 are placed around the annulus of the valve beginning with the fibrous trigone 182 and proceeding around the posterior annulus of the opposite fibrous trigone 184. The sutures 180 are then passed through the annuloplasty band 186 which is attached to a band holder or stent 188.

Figure 17:
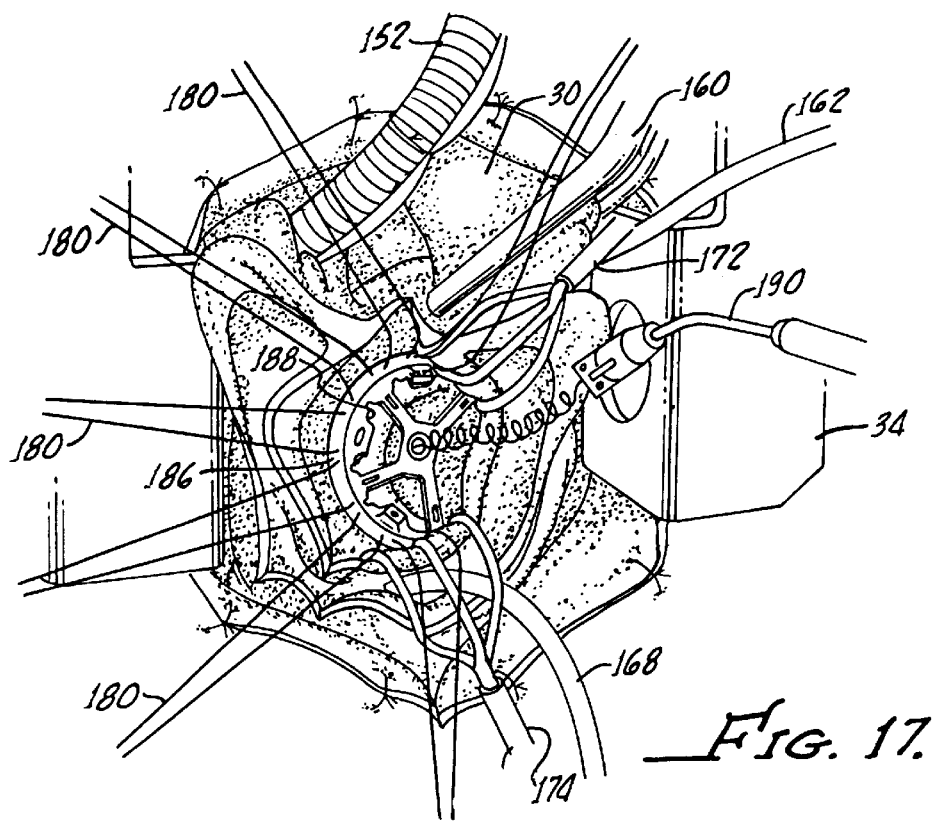
FIG. 17 is a pictorial illustration of the performance of an annuloplasty in the surgical field of FIG. 15.
Figure 18:
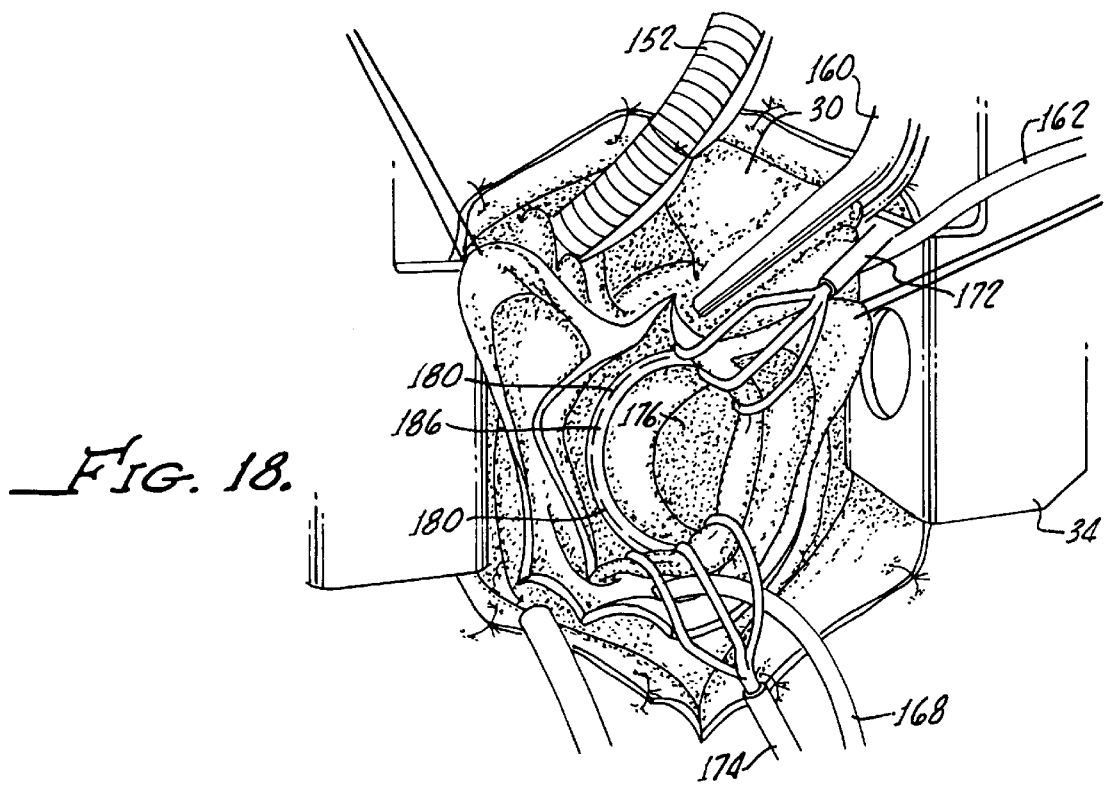
FIG. 18 is a pictorial illustration of the completion of an annuloplasty in the surgical field of FIG. 15.

Referring to FIGS. 17 and 18, once placement of the sutures is complete, the handle 190 of the stent 188 is released and the stent 188 with the annuloplasty band 186 is guided into position proximal to the mitral valve 176. The sutures 180 are tightened and tied down thereby securing the annuloplasty band 186 into place. The stent 188 is then released and removed from the band 186 thus leaving the repaired valve 176.

It is appreciated that the use of other types of annuloplasty rings are contemplated in the just-described surgery. For example, annuloplasty rings that requires suturing around the entire periphery of the ring (e.g., a Carpentier ring or a Duran ring) may be used without departure from the invention.

Figure 19:
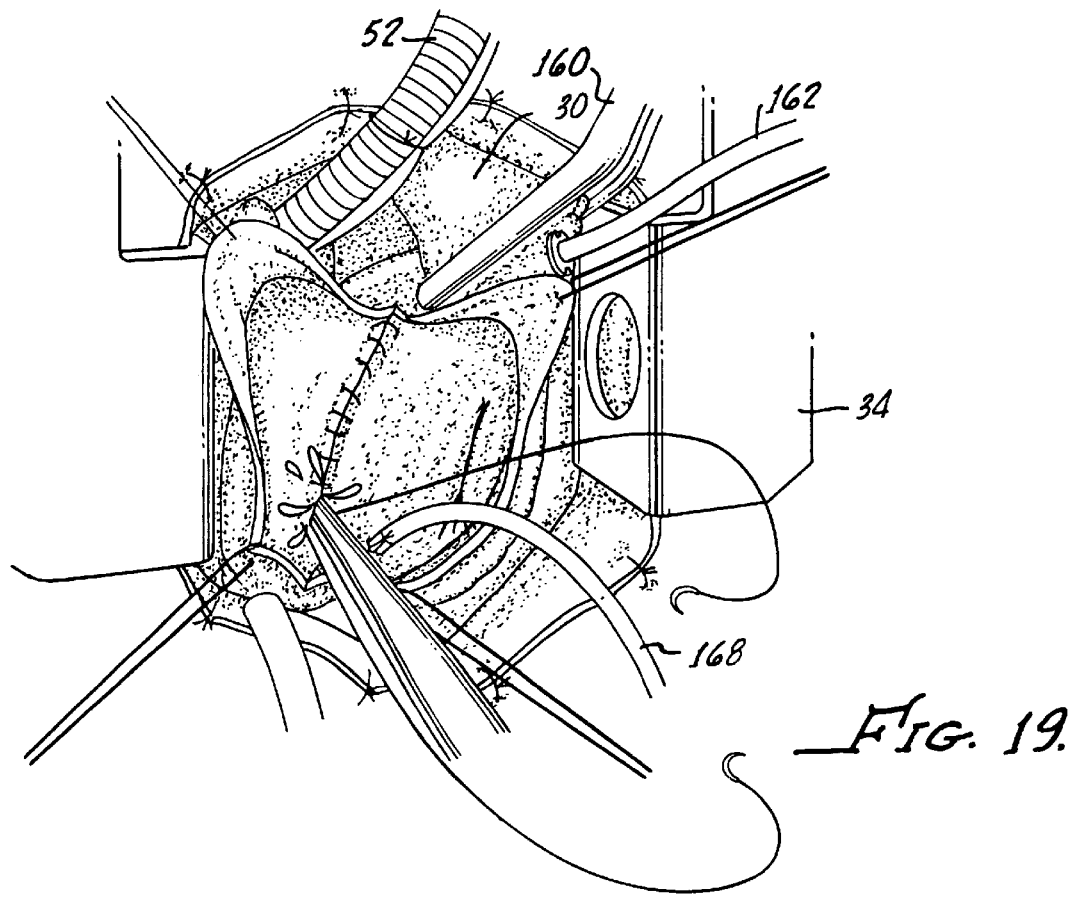
FIG. 19 is a pictorial illustration of the closure of the inter-atrial wall as incised in FIG. 14.

Referring to FIG. 19, the incision 170 into the interatrial septum is sutured 192 back together using continuous 4-0 Prolene or other suitable suture material. Attempts are made to remove all air from the left atrium and then the sutures 192 are tightened and tied down.

De-airing of the left ventricle is also effected at this time. In that connection, just prior to release of the aortic clamp 160, gentle suction may be applied on the cardioplegia cannula 162 in the ascending aorta 30. Weaning from the cardiopulmonary bypass is then initiated. The retrograde cardioplegia cannula 168 is removed as is the aortic clamp 162, thereby restoring blood flow. The lungs are then inflated until blood flows through the sutures 192. Suction through the cardioplegia cannula may continue as needed after the aortic clamp 162 is removed.

Figure 20:
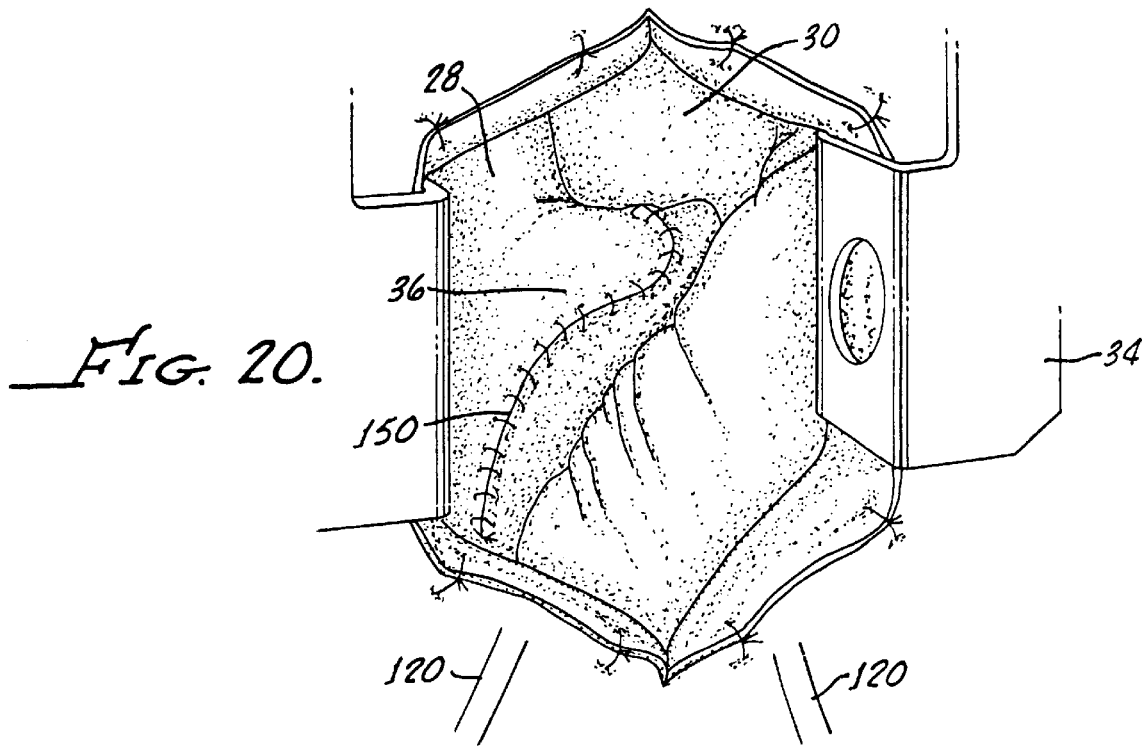
FIG. 20 is a pictorial illustration of the closure of the right atrium as shown incised in FIG. 15.

Referring to FIG. 20, the incision 150 in the right atrium is also closed using continuous 4-0 Prolene or other suitable suture material. Simultaneously, the heart is being observed to ensure a return to normal cardiac function and to ensure the absence of air bubbles within the heart chambers. If the heart function returns properly, the cannulae are removed and the incisions from the cannulae placement are repaired as needed and sutured shut.

Four pacemaker wires 120 are placed percutaneously through the chest onto the atrium and the ventricle to facilitate temporary pacing should it be necessary. Conventional pleural chest tubes as depicted in FIG. 11 may also be placed in the chest. The wound is then closed by suitably reappoximating the muscle, subcutaneous tissue and the skin, in layers.

Figure 21:
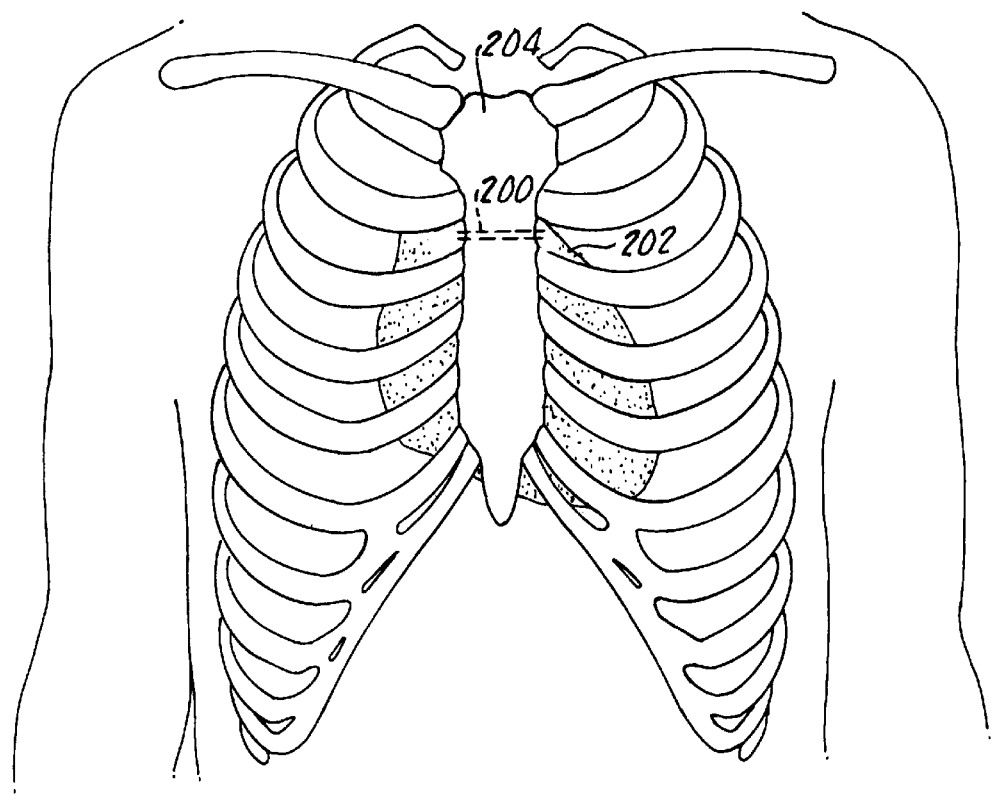
FIG. 21 is a pictorial illustration of a transverse incision across the sternum.

Referring to FIG. 21, in another approach to minimally invasive surgery in accordance with the present invention, the patient is anesthetized in the supine position and intubated. Defibrillator patches (not shown) are placed on the patient's back and anterior left chest wall. A transesophageal cardiography probe (not shown) is placed to assess the etiology of the tissue requiring surgery, which by way of example only, is the aortic valve in this embodiment. The cardiography probe is also useful in the removal of air from the heart prior to completion of the surgery.

Figure 22:
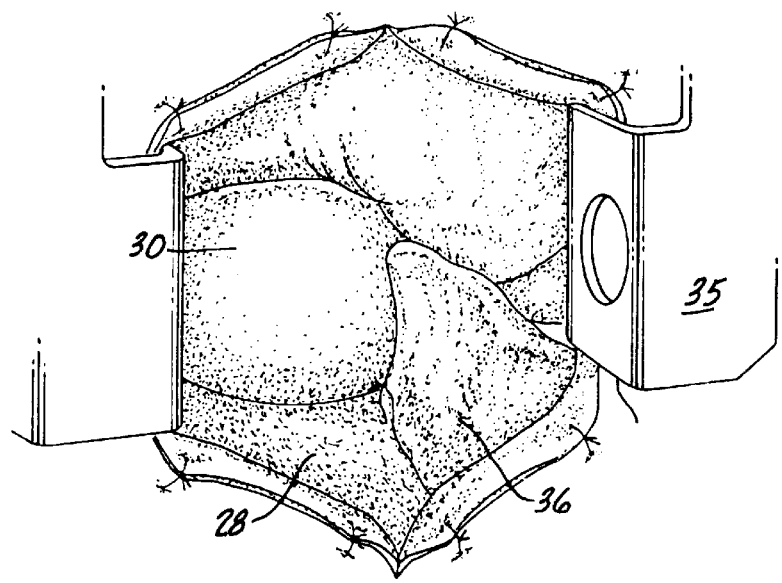
FIG. 22 is a pictorial illustration of the exposed surgical field of the incision of FIG. 21.

Referring to FIGS. 21 and 22, a 10 cm transverse incision is made over the second intercostal space. In certain circumstances, it may be appropriate to make the incision over the third intercostal space, depending on the location of the targeted surgical area. The subcutaneous tissue and pectoralis muscles are divided. The internal thoracic artery (not shown) is ligated and divided bilaterally. The tissue is retracted and draped back to better expose the surgical area. A sternal saw (not shown) is then used to divide the sternum 204 transversely in alignment with the original incision 200. A retractor 35, such as a Finochietto retractor, is placed between the two bisected portions of the sternum 204 and the sternum opened. The separation of the sternum 204 and the subsequent cutting and retracting of the pericardium exposes the entire ascending aorta 30, the superior vena cava 28 and the tip of the right atrial appendage 36.

Referring to FIG. 23, the patient is cannulated for heart bypass by inserting an arterial return cannula 206 directly into the ascending aorta 30 and a venous drain cannula 208 into the superior vena cava 28. A venous drain cannula 210 is also inserted into the inferior vena cava through a percutaneous incision 212 proximal to the original incision opening.

Once cannulation is completed, the aorta 30 is occluded at a position proximal, of the brachycephalic artery and distal of the coronary ostia 222 with a cross-clamp 216 and bypass of blood flow around the heart is initiated. As discussed previously, an aortic occlusion balloon inserted through a femoral artery or sub-clavian artery could also be used to block the aorta 30. A transverse incision 218 is made in the aorta 30 from a position proximal to the clamp 216 into the noncoronary cusp 220, which incision exposes the coronary ostia 222 and the aortic valve 224.

Figure 24:
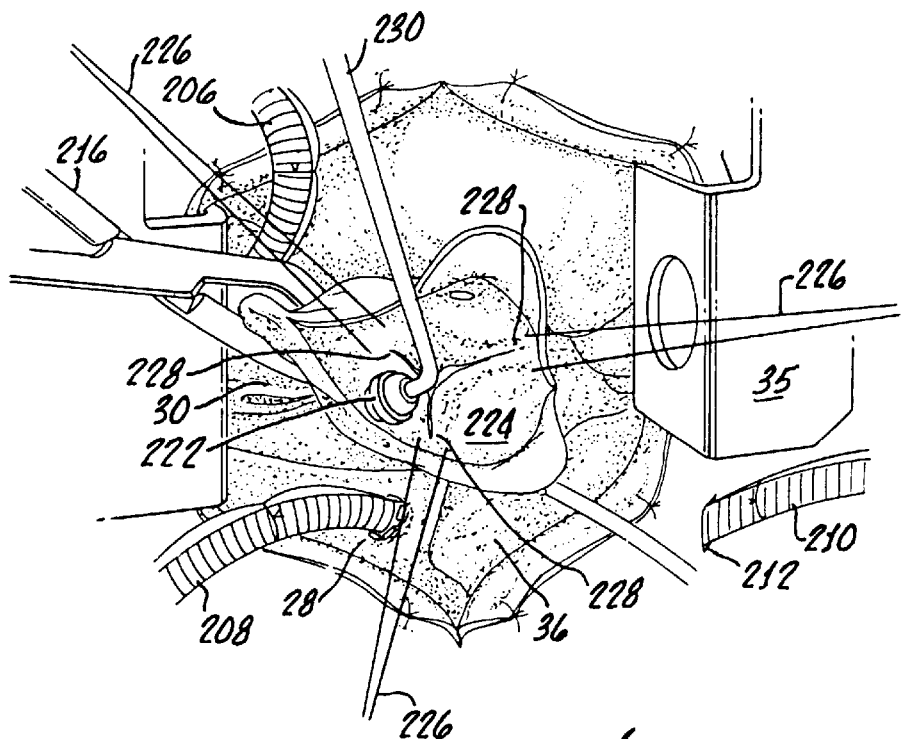
FIG. 24 is a pictorial illustration of a surgical procedure on the aortic valve in the surgical field of FIG. 22.

Referring to FIG. 24, sutures 226 are placed at the top of each commissure 228 of the valve 224 and draped under tension outside the wound so as to elevate the valve 224, retract the aorta 30 and give a normal anatomical orientation to the aortic root. Cardioplegia is then introduced into one of the coronary ostia 222 with an antegrade cardioplegia catheter 230. The cardiac activity of the heart then progressively diminishes until the heart ceases beating altogether.

Referring to FIG. 25, replacement of the aortic valve is effected by excising the native aortic valve tissue and placing sutures 232 around the annulus of the aortic root. The sutures 232 are then placed through the sewing ring of the aortic valve prosthesis 234 which is attached to a valve holder 236. The prosthesis 234 is then guided into location, the sutures 232 tightened and tied and the holder 236 removed.

Referring to FIGS. 25 and 26, the sutures 226 through the commissures 228 are maintained in tension until closure of the aorta 30 is begun in order to enable proper exposure of the field. Closure of the aorta 30 is begun by applying a single layer of 4-0 Prolene or other suitable material to bring the edges of the incision together. The sutures 226 attached to the commissures 228 are then cut.

Prior to completion of the closure of the aorta 30, care is taken to remove air from the left ventricle. The lungs are inflated and blood is allowed to flow into the aorta 30 by releasing the clamp 216 which enables air to escape through the remaining open portion of the incision, which portion is held open with a tool 240. The completeness of the air removal is monitored by echocardiography.

Figure 27:
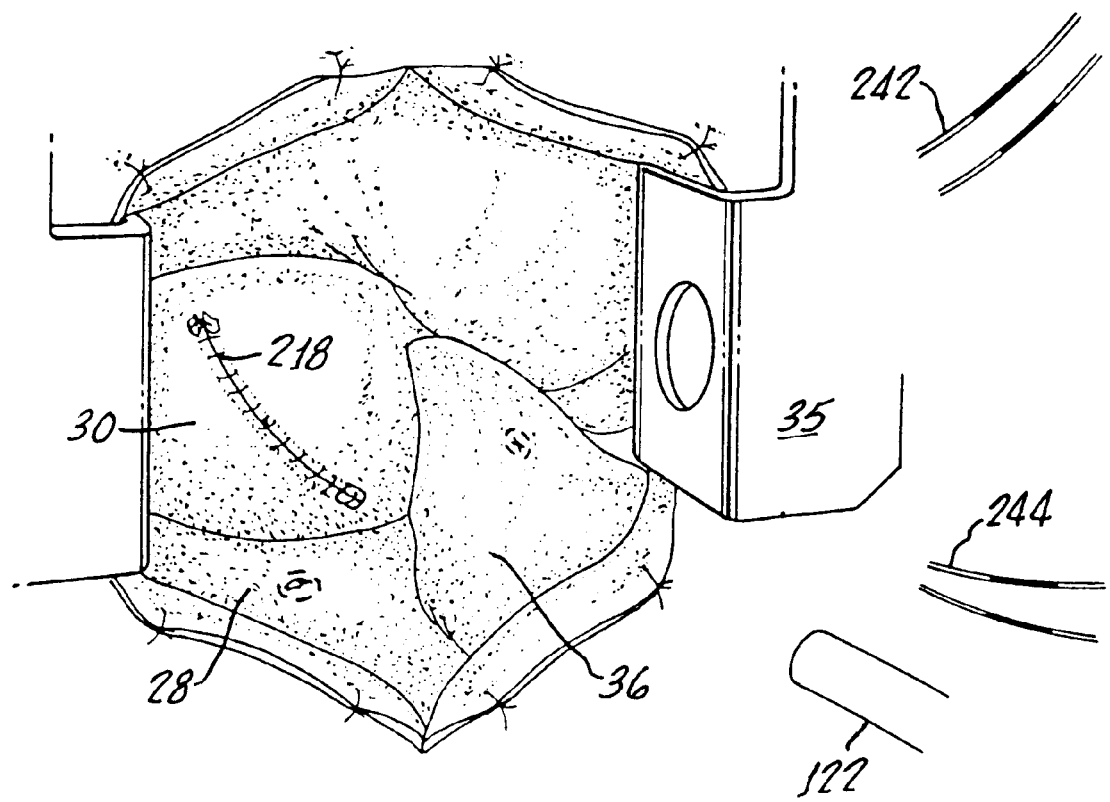

Referring to FIG. 27, the patient is further weaned from bypass and closure of the incision 218 is completed. Assuming normal cardiac function returns, the patient is then decannulated and the wounds from the cannulation repaired and closed. Two atrial and two ventricular pacing wires 242, 244 are placed percutaneously into the chest for pacing the heart if necessary. A pleural chest tube 122 is also placed in the chest.

The retractor 35 is then removed and the sternum 204 is closed with monofilament wire or any other suitable material. The incision 200 is then closed by reapproximating the muscles, the subcutaneous tissue and skin, in layers.

The minimally invasive valve surgery in accordance with the present invention simplifies the cardiac surgery for surgeons and provides beneficial results for patients. The operative procedure allows for a relatively small, e.g., ten centimeter, incision that makes opening and closing of the chest easier and faster without compromising the surgical exposure or access to the surgical area. Performing repairs or replacements through an incision in accordance with the present invention simplifies the surgical technique without increasing the difficulty of the procedure or the technical ability required to perform aortic valve surgery. Further, the smaller incision employed in the procedure results in less bleeding, and a lesser area to become infected.

Moreover, not only does the smaller incision tend to cause less incisional pain in patients, the absence of traumatic retraction and the strain placed on the ribs from a gross thoracotomy tends to also account for lower incisional pain. Without incisional pain, patients require less postoperative analgesia and are more easily ambulated allowing for earlier discharge from the hospital. Decreased patient morbidity as a result of decreased postoperative discomfort tends to result in shorter length of hospital stays.

The foregoing is a description of preferred exemplary embodiments and best mode of the invention contemplated by applicant at time of filing the application. The invention is not limited to the specific embodiments shown. Rather, the scope of the invention is expressed in the appended claims.

What is claimed is:

1. A method for minimizing invasion in a mitral valve repair or replacement procedure, comprising:

making a parasternal incision exposing a predetermined number of costal cartilages;

excising at least one costal cartilage and exposing the right atrium;

incising the right atrium and intra-atrial septum to provide access to an area adjacent the mitral valve; and performing a mitral valve repair or replacement procedure.

2. The method of claim 1, further comprising:

after excising at least one costal cartilage to expose the right atrium, providing downward traction on the left atrial wall using a deformable retractor.

3. The method of claim 2, wherein the deformable retractor comprises a flat elongate band that may be manipulated into different shapes.

4. The method of claim 1, further comprising:

after excising at least one costal cartilage to expose the right atrium, inserting a resilient ring member into the surgical field between the mitral valve and the left atrial wall to facilitate lifting tissue away from the valve area needing repair.

5. The method of claim 4, wherein the resilient ring member is flexible.

6. The method of claim 1 wherein the step of making a parasternal incision comprises making a right parasternal incision extending from the vicinity of the lower edge of the second costal cartilage to the superior edge of the fifth costal cartilage.

7. The method of claim 1 wherein the step of making a parasternal incision comprises making an incision approximately 10 cm in length within a region on the chest that enables direct access to a location in the heart approximately 3 cm above the supra annular ridge and in the mid-ventricular cavity.

8. The method of claim 1 wherein the step of making a parasternal incision comprises making an incision approximately 10 cm in length within a substantially rectangular area on the chest extending approximately two inches on either side of the sternum and from no higher than the first intercostal space at the top to the sixth intercostal space at the bottom.

9. The method of claim 1, wherein the step of exposing comprises:

dividing the outer layer of muscle tissue below the skin;

exposing one or more costal cartilages;

resecting the exposed costal cartilages; and incising and retracting the pericardium.

10. The method of claim 1 wherein the step of performing a mitral valve repair or replacement procedure comprises the steps of:

occluding the aorta to facilitate establishing a coronary by-pass;

arresting the heart; and establishing cardiopulmonary bypass using at least one blood conduit placed within the area adjacent the mitral valve.

11. The method of claim 1 wherein the step of performing a mitral valve repair or replacement procedure comprises implanting a prosthetic valve.

12. The method of claim 1 wherein the step of performing a mitral valve repair or replacement procedure comprises implanting an annuloplasty band.

* * * * *